US007547447B2

(12) United States Patent
Yiu et al.

(10) Patent No.: US 7,547,447 B2
(45) Date of Patent: Jun. 16, 2009

(54) BIOARTIFICIAL LACRIMAL GLAND

(75) Inventors: Samuel C. Yiu, Marina del Rey, CA (US); Austin K. Mircheff, La Crescenta, CA (US); Ronald E. Smith, Los Angeles, CA (US); Jean Jacob, New Orleans, LA (US); Mel Trousdale, Pasadena, CA (US)

(73) Assignees: Doheny Eye Institute, Los Angeles, CA (US); The Board of Supervisors of Louisiana State University and Agriculture and Mechanical College, New Orleans, LA (US)

( * ) Notice: Subject to any disclaimer, the term of this patent is extended or adjusted under 35 U.S.C. 154(b) by 353 days.

(21) Appl. No.: 10/990,359

(22) Filed: Nov. 15, 2004

(65) Prior Publication Data

US 2006/0104957 A1  May 18, 2006

(51) Int. Cl.
*A61F 2/00* (2006.01)
(52) U.S. Cl. .................. 424/423; 424/427; 424/422; 424/93.7; 435/371
(58) Field of Classification Search .................. 424/423
See application file for complete search history.

(56) References Cited

U.S. PATENT DOCUMENTS

| 6,331,313 | B1 | 12/2001 | Wong et al. |
| 6,743,626 | B2 | 6/2004 | Baum et al. |
| 2003/0031696 | A1 | 2/2003 | Baum et al. |

FOREIGN PATENT DOCUMENTS

WO    WO 00/50049 A2    8/2000

OTHER PUBLICATIONS

Casbon et al., "Prolactin inhibits carbachol-dependent secretion by lacrimal acinar cells in vitro," *Adv. Exp. Med. Biol.* 506(Pt A):231-235 (2002).
Hann et al., "Influence of culture conditions on the androgen control of secretory component production by acinar cells from the rat lacrimal gland," *Invest. Ophthalmol Vis. Sci.* 32(9):2610-2621 (1991).
Hann et al., "Morphology and function of lacrimal gland acinar cells in primary culture," *Invest Ophthalmol. Vis. Sci.* 30(1):145-158 (1989).
Huang et al., "Analysis of cytomegalovirus infection and replication in acinar epithelial cells of the rat lacrimal gland," *Invest. Ophthalmol. Vis. Sci.* 37(6):1174-1186 (1996).
Stevenson et al., "A new model system for studying lacrimal physiology using cultured lacrimal gland acinar cells on Matrigel® rafts," *Adv. Exp. Med. Biol.* 506(Pt A):159-163 (2002).
Vanaken et al., "Primary rat lacrimal cells undergo acinar-like morphogenesis on reconstituted basement membrane and express secretory component under androgen stimulation," *Exp. Cell. Res.* 238(2):377-388 (1998).

Yoshino, K., "Establishment of a human lacrimal gland epithelial culture system with in vivo mimicry and its substrate modulation," *Cornea* 19(Suppl. 1):S26-S36 (2000).
Yoshino, K., "Substrate modulation of morphology, growth, and tear protein production by cultured human lacrimal gland epithelial cells," *Exp. Cell. Res.* 220(1):138-151 (1995).
Aframian et al., "Absence of tight junction formation in an allogeneic graft cell line used for developing an engineered artificial salivary gland," *Tissue Eng.* 8(5):871-878 (2002).
Aframian et al., "The growth and morphological behavior of salivary epithelial cells on matrix protein coated biodegradable substrata," *Tissue Eng.* 6:209-216 (2000).
Agre et al., "The aquaporins, blueprints for cellular plumbing systems," *J. Biol. Chem.* 273(24):14659-14662 (1998).
Baum, "Principles of saliva secretion," *Ann. NY Acad. Sci.* 694:17-23 (1993).
Baum, "Prospects for Re-engineering Salivary Glands," *Adv. Dent. Res.* 14:84-88 (2000).
Cao et al., "Transplantation of chondrocytes utilizing a polymer cell construct to produce tissue-engineered cartilage in the shape of a human ear," *Plast. Reconstr. Surg.* 100(2):297-304 (1997).
Davis and Vacanti, "Toward development of an implantable tissue engineered liver," *Biomaterials* 17 (3):365-372 (1996).
Guo et al., "Lacrimal gland epithelial cells stimulate proliferation in autologous lymphocyte preparations," *Exp. Eye. Res.* 71(1):11-22 (2000).
Johnson and Murphy, "Changes in the tear film and ocular surface from dry eye syndrome," *Prog. Retin. Eye Res.* 23(4):449-474 (2004).
Kim and Mooney, "Development of biocompatible synthetic extracellular matrices for tissue engineering," *Trends Biotechnol.* 16(5):224-230 (1998).
Kim et al., "Engineered smooth muscle tissues: regulating cell phenotype with the scaffold," *Exp. Cell Res.*: 251(2):318-328 (1999).
Kleinman et al., "Isolation and characterization of type IV procollagen, laminin, and heparan sulfate proteoglycan from the EHS sarcoma," *Biochem.* 21(24):6188-6193 (1982).
Langer and Vacanti, "Tissue engineering," *Science* 260(5110):920-926 (1993).
Meneray et al. "Morphology and physiologic responsiveness of cultured rabbit lacrimal acini," *Invest. Ophthalmol. Vis. Sci.* 35(12):4144-4158 (1994).
Mostov et al., "Membrane traffic in polarized epithelial cells," *Curr. Opin. Cell Biol.* 12(4):483-490 (2000).
Nerem and Sambanis, "Tissue engineering: From biology to biological substitutes," *Tissue Engineering* 1(1):3-13 (1995).
Nguyen et al., "Characterization of immortalized rabbit lacrimal gland epithelial cells," *In Vitro Cell Dev. Biol. Anim.* 35(4):198-204 (1999).

(Continued)

*Primary Examiner*—Ralph Gitomer
*Assistant Examiner*—Tiffany M Gough
(74) *Attorney, Agent, or Firm*—McDermott Will & Emery LLP

(57) ABSTRACT

The present invention provides a bioartificial lacrimal gland which contains at least one unit that includes (a) a permeable housing having an interior and an exterior; (b) an outlet connecting the housing interior to the housing exterior; and (c) a population of lacrimal epithelial cells within the housing interior.

60 Claims, 5 Drawing Sheets

OTHER PUBLICATIONS

Oberpenning et al., "De novo reconstitution of functional mammalian urinay bladder by tissue engineering," *Nat. Biotechnol.* 17:149-155 (1999).

Pastan and Bailey, "Dialysis therapy," *New Engl. J. Med.* 338(20):1428-1437 (1998).

Saarloos et al., "Intermediate filament, laminin and integrin expression in lacrimal gland acinar cells: Comparison of an immortalized cell line to primary cells, and their response to retinoic acid," *Curr. Eye Res.* 19(5):439-449 (1999).

Schaumberg et al., "Epidemiology of dry eye syndrome," *Adv. Exp. Med. Biol.* 506 (Part B):989-998 (2002).

Schechter et al., "Growth of purified lacrimal acinar cells in matrigel raft cultures," *Exp. Eye Res.* 74:349-360 (2002).

Schonthal et al., "Proliferation of lacrimal gland acinar cells in primary culture. Stimulation by extracellular matrix, EGF, and DHT," *Exp Eye Res.* 70(5):639-649 (2000).

Sheridan et al., "Bioabsorbable polymer scaffolds for tissue engineering capable of sustained growth delivery," *J. Control. Rel.* 64:91-102 (2000).

Smith, Slide presentation at the American Academy of Ophthalmology 2003 Annual Meeting, Nov. 17, 2003.

Tsubota, "Understanding dry eye syndrome. Lacrimal Gland, Tear Film, and Dry Eye Syndromes 3 Basic Science and Clinical Relevance," *Adv. Med. Biol.* 506 (Part A):3-16 (2002).

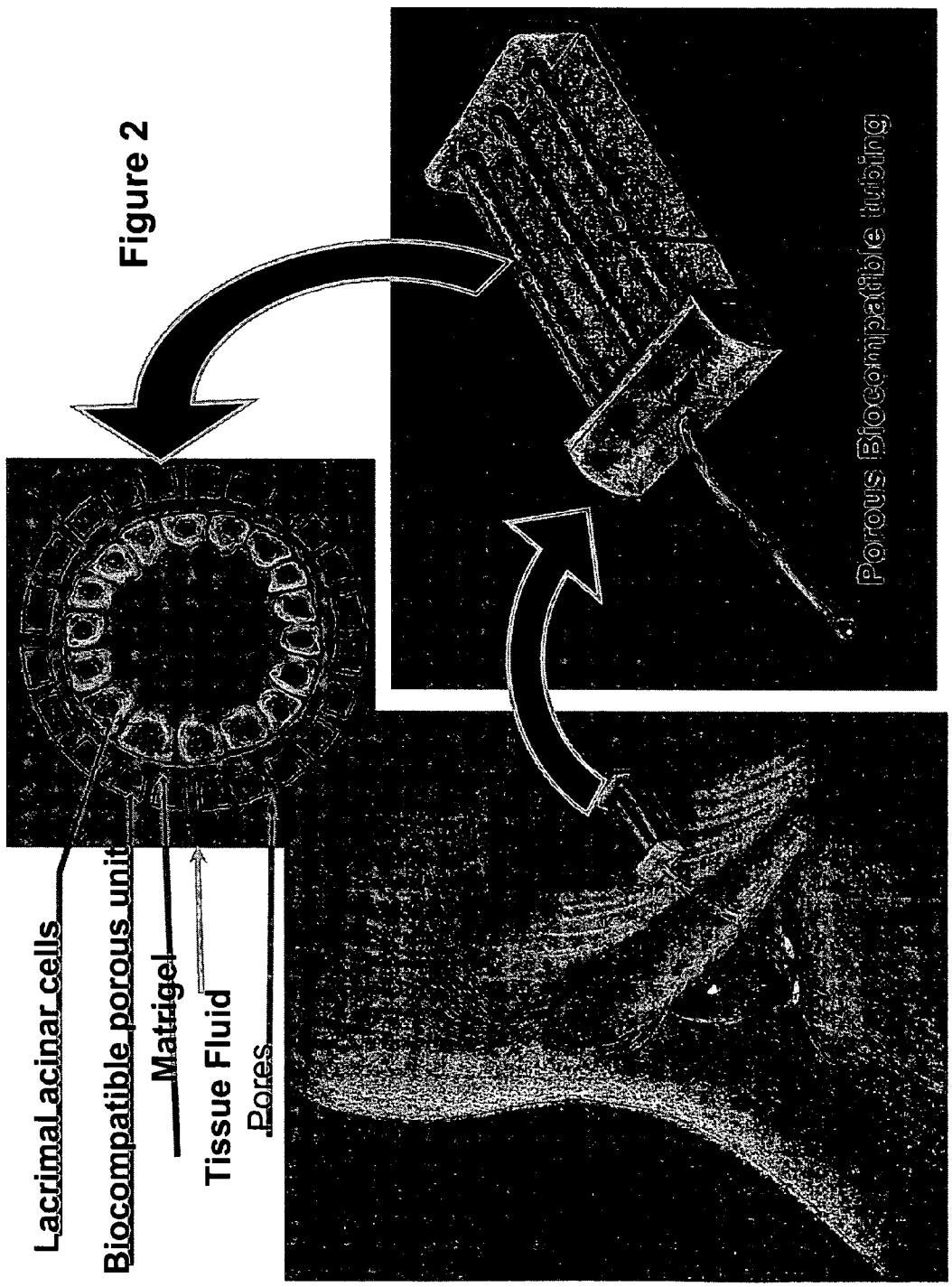

BIOARTIFICIAL LACRIMAL GLAND

This invention was made with government support under Grant 15457 awarded by the National Eye Institute. The government has certain rights in this invention.

BACKGROUND OF THE INVENTION

1. Field of the Invention

The present invention relates generally to ophthalmology and tissue engineering and, more specifically, to bioartificial, fluid-secreting lacrimal glands which can be useful in treating individuals with dry eye or other disorders of the lacrimal gland.

BACKGROUND INFORMATION

Dry eye syndrome results from a decline in either the quality or the quantity of fluid that forms the tear film of the ocular surface. The patient with dry eye syndrome experiences constant pain from eye irritation including a sandy or gritty sensation which, if left untreated, can lead to scarring or ulceration of the cornea, infection and possible loss of vision. Dry eye syndrome, which occurs in about 10 million Americans, results from the normal aging of tear glands as well as disorders which cause changes in the amount and content of tears produced. Although dry eye can occur at any age, most cases are due to normal aging of the tear glands, with an estimated nearly 75% of people over the age of 65 experiencing dry eye syndrome. Dry eye syndrome is most common in women who are pregnant or postmenopausal; individuals with Sjögren's syndrome; and those suffering from allergies or wearing contact lenses.

In the early stages of dry eye syndrome, symptoms may be intermittent. However, symptoms generally become more persistent as dry eye worsens. If dry eye is not treated properly, corneal scarring may result, potentially leading to a decrease in visual acuity which may daily functional activity.

Unfortunately, most current treatments for dry eye syndrome only give temporary relief and seldom arrest or reverse damage to the eye. Dry eye syndrome is typically treated by application of artificial tears and ointments, with some forms of dry eye benefiting from the placement of plugs in the ducts that drain tears from the eye. For severe forms of dry eye, special goggles, called moisture-chamber spectacles, can be worn. Recently, the topical cyclosporine Restasis, which may inhibit the inflammatory nature of some forms of dry eye syndrome, has been indicated for the treatment of this disorder. However, only patients with moderately dry eyes will benefit from this treatment; in particular, patients with non-functioning lacrimal glands will not benefit from Restatsis treatment. Thus, there is a need for innovative devices and methods for providing long-term relief and for treating severe forms of dry eye syndrome as well as other disorders of the lacrimal glands or blocked ducts such as Stevens-Johnson syndrome, chemical and thermal injuries to the eye, and ocular cicatricial pemphigoid. The present invention satisfies these needs and provides related advantages as well.

SUMMARY OF INVENTION

The present invention provides a bioartificial lacrimal gland which contains at least one unit that includes (a) a permeable housing having an interior and an exterior; (b) an outlet connecting the housing interior to the housing exterior; and (c) a population of lacrimal epithelial cells within the housing interior. In one embodiment, a bioartificial lacrimal gland of the invention is characterized by directional fluid secretion in which fluid exits from the housing interior through the outlet. The directional fluid secretion rate can be, for example, at least 6.5 µl/cm$^2$/hour.

Further provided herein is a method of treating or reducing the severity of a disorder resulting from lacrimal gland dysfunction in an individual by implanting into the individual a bioartificial lacrimal gland that includes at least one unit containing (a) a permeable housing having an interior and an exterior; (b) an outlet connecting the housing interior to the housing exterior; and (c) a population of lacrimal epithelial cells within the housing interior.

BRIEF DESCRIPTION OF THE DRAWINGS

FIG. 2 shows several views of a bioartificial lacrimal gland. (A) Cartoon of bioartificial lacrimal gland implantation. (B) Schematic of bioartificial lacrimal gland having three units held in a unit support. The permeable tubular housing of each unit is illustrated. (C) Cross-sectional view of a single unit of a bioartificial lacrimal gland showing the permeable housing, MATRIGEL™ substratum, and laminar epithelial cells. The schematic further illustrates the site of entry of tissue fluid through pores of the permeable housing.

DETAILED DESCRIPTION OF THE INVENTION

Figure 1A:
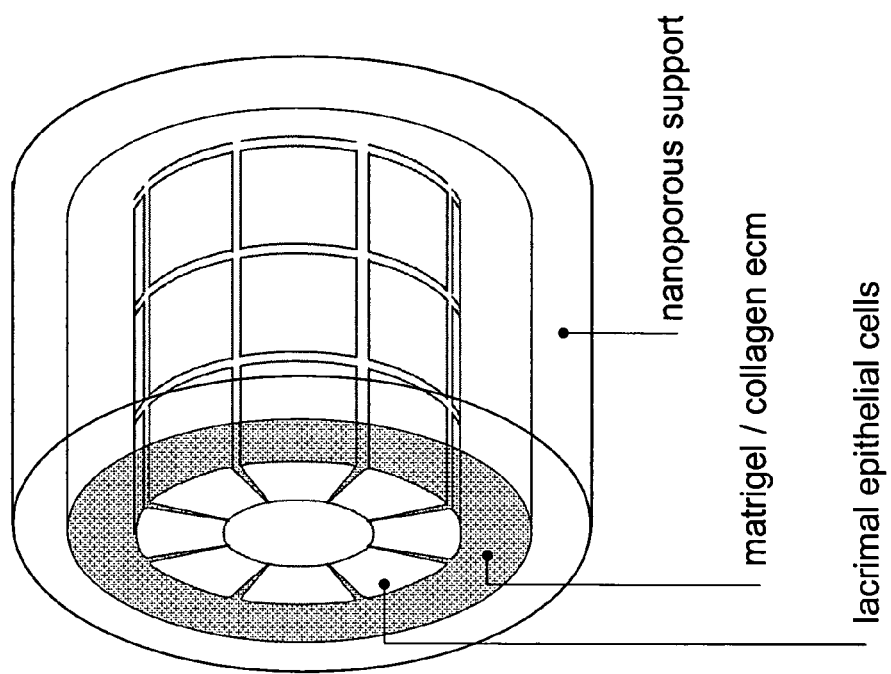
FIG. 1 shows a bioartificial lacrimal gland having a single unit containing a tubular permeable housing; viscous substratum of MATRIGEL™; and population of lacrimal epithelial cells. (A) Side view. (B) Cross-sectional view.

The present invention provides a bioartificial lacrimal gland which contains at least one unit that includes (a) a permeable housing having an interior and an exterior; (b) an outlet connecting the housing interior to the housing exterior; and (c) a population of lacrimal epithelial cells within the housing interior. In one embodiment, a bioartificial lacrimal gland of the invention is characterized by directional fluid secretion in which fluid exits from the housing interior through the outlet. The directional fluid secretion rate can be, for example, at least 6.5 µl/cm$^2$/hour.

Any of a variety of permeable housings are useful in a bioartificial lacrimal gland of the invention. In one embodiment, a bioartificial lacrimal gland of the invention includes a permeable housing which has a concave interior surface. Such a permeable housing can have, for example, a substantially cylindrical interior surface or a substantially spherical interior surface and further can be, for example, substantially tubular.

In one embodiment, the permeable housing included in a bioartificial lacrimal gland of the invention is a tube. In another embodiment, the permeable housing is a tube having a first closed end and a second end which is the outlet connecting the housing interior to the housing exterior. Where the permeable housing of a bioartificial lacrimal gland is tubular, the tube can have a lumen, for example, of uniform diameter. In particular embodiments, the lumen of the tube has a diameter of no more than 2 mm or a diameter of between 0.1 and 0.5 mm. In further embodiments, the length of the tube is at most 10 mm or at most 5 mm. A permeable housing useful in the invention can be, for example, a porous housing having any of a variety of pore sizes including, without limitation, a pore size of between 0.01 and 10 microns or a pore size of between 0.1 and 5 microns.

Permeable housings useful in the invention can be composed of any of a variety of biomaterials including, but not limited to, polymeric biomaterials such as homopolymeric and copolymeric biomaterials; non-biodegradable biomaterials and biodegradable biomaterials. As non-limiting examples, a permeable housing useful in the invention can include a biomaterial such as polysiloxane; polydimethylsiloxane; polyurethane; polyvinylpyrrolidone; polymethacrylate; polyvinyl alcohol; polyethylene; polyethylene glycol; poly(glycolic acid); poly(L-lactic acid); poly(lactic-co-glycolic acid); collagen; cellulose; or a copolymer or derivative thereof. As further non-limiting examples, a permeable housing useful in the invention can include at least 90% of one of the following biomaterials: polysiloxane; polydimethylsiloxane; polyurethane; polyvinylpyrrolidone; polymethacrylate; polyvinyl alcohol; polyethylene; polyethylene glycol; poly(glycolic acid); poly(L-lactic acid); poly(lactic-co-glycolic acid); collagen; cellulose; or a copolymer or derivative thereof.

A bioartificial lacrimal gland of the invention optionally includes a viscous substratum within the housing interior. In one embodiment, the viscous substratum is adhered to the interior surface of the permeable housing. A viscous substratum useful in the invention can be, for example, a gel such as a hydrogel and further can include, without limitation, collagen, hydroxymethylcellulose, hyaluronan, or a copolymer or derivative thereof A viscous substratum useful in the invention also can include, for example, one or more other extracellular matrix components such as MATRIGEL™. In one embodiment, the viscous substratum includes MATRIGEL™ at a final concentration of 0.25 to 5 mg/ml. In another embodiment, the viscous substratum includes MATRIGEL™ at a final concentration of 0.25 to 5 mg/ml and further includes fetal bovine serum.

In a bioartificial lacrimal gland of the invention, the lacrimal epithelial cells can be polarized and, further, can be arrayed in a polarized monolayer. Such a polarized monolayer of lacrimal epithelial cells optionally can be adhered to the viscous substratum. Any of a variety of lacrimal epithelial cells are useful in the bioartificial glands of the invention including, without limitation, primary cells, established cells, transfected cells, human cells, primate cells, rabbit cells, and goose cells. In one embodiment, the population of lacrimal epithelial cells is a population of human lacrimal epithelial cells. In another embodiment, the population of lacrimal epithelial cells is a population of rabbit lacrimal epithelial cells.

A variety of additional components optionally can be included in a bioartificial gland of the invention. As non-limiting examples, a bioartificial gland of the invention can include at least one growth factor or immunosuppressive agent. In particular embodiments, a bioartificial lacrimal gland of the invention includes HEPATO STIM® Culture Medium, epidermal growth factor or nerve growth factor. In another embodiment, a bioartificial lacrimal gland of the invention includes fetal bovine serum at a concentration of 10% and epidermal growth factor at a concentration of 5 ng/ml.

A bioartificial lacrimal gland of the invention optionally includes a gate which is joined to the outlet connecting the housing interior to the housing exterior. Such a gate can be, for example, responsive to a stimulus. If desired, a bioartificial lacrimal gland of the invention further can include an encapsulating membrane which is impermeable to antibodies and immune cells.

A bioartificial lacrimal gland of the invention can include a single unit or can include a plurality of units, where each unit contains (a) a permeable housing having an interior and an exterior; (b) an outlet connecting the housing interior to the housing exterior; and (c) a population of lacrimal epithelial cells within the housing interior. In one embodiment, a bioartificial lacrimal gland of the invention has at least three units. In another embodiment, a bioartificial lacrimal gland of the invention has at least five units. In a further embodiment, a bioartificial lacrimal gland of the invention additionally includes a unit support which holds each of the plurality of units in a defined configuration. In yet another embodiment, a bioartificial lacrimal gland of the invention includes a unit support which holds each of the plurality of units substantially in parallel. Any of the above bioartificial lacrimal glands of the invention may optionally include an encapsulating membrane which is impermeable to antibodies and immune cells.

In a bioartificial lacrimal gland of the invention including a plurality of units, the permeable housing can be, without limitation, a tube and additionally can be a tube having a first closed end and a second end which is the outlet. Furthermore, in a bioartificial lacrimal gland of the invention including a plurality of tubes having first closed ends and second ends which are outlets, the gland can further include a common duct which is joined to each of the outlets. In one embodiment, the common duct further includes a gate which optionally can be responsive to a stimulus. In another embodiment, a bioartificial lacrimal gland of the invention includes an encapsulating membrane which is impermeable to antibodies and immune cells.

As is well known in the art, the cells of a tissue-engineered organ capable of fluid secretion generally are capable of attaining and maintaining a polarized monolayer organization (Aframian et al., *Tissue Eng.* 8(5):871-8. (2002)). Furthermore, to secrete fluid unidirectionally, secretory cells generally express an asymmetric distribution of transport proteins which generate an osmotic gradient to provide a facilitated water permeability pathway (Baum et al., *Ann. NY Acad. Sci.* 694:17-23 (1993); Mostov et al., *Curr. Opin. Cell Biol.* 12:483-490 (2000); and Agre et al., *J. Biol. Chem.* 273:14659-14662 (1998)). The asymmetric distribution of membrane proteins is due, at least in part, to demarcation of apical and basolateral membrane domains by tight junctions.

A bioartificial lacrimal gland of the invention can ameliorate, at least in part, dry eye syndrome and other disorders resulting from lacrimal gland dysfunction by providing supplemental fluid secretion. In a bioartificial lacrimal gland of the invention, the lacrimal epithelial cells can be polarized as in a native gland; such polarized cells are characterized by apical concentrations of secretory granules, junctional complexes at the apical-lateral cell surfaces, and basal nuclei and basal lamellae of the endoplasmic reticulum.

A bioartificial lacrimal gland of the invention can be functionally characterized by producing a directional fluid secretion rate of, for example, at least 6.5 $\mu l/cm^2/hour$. Furthermore, as non-limiting examples, a bioartificial lacrimal gland of the invention can be functionally characterized by producing a directional fluid secretion rate of, for example, at least 2, 3, 4, 5, 6, 7, 8, 9, 10, 12, 14, 16, 18 or 20 $\mu l/cm^2/hour$. As disclosed further below, the directional fluid secretion rate can be produced by a bioartificial gland which has a single permeable housing unit including an outlet and population of lacrimal epithelial cells within the housing interior, or can accrue from a bioartificial gland which contains a plurality of such units.

A bioartificial lacrimal gland of the invention contains at least one unit which includes (a) a permeable housing having an interior and an exterior; (b) an outlet connecting the housing interior to the housing exterior; and (c) a population of lacrimal epithelial cells within the housing interior. As used herein, the term "unit" is synonymous with "unit of a bioartificial lacrimal gland" or "gland unit" and, at a minimum, contains (a) a permeable housing having an interior and an exterior; (b) an outlet connecting the housing interior to the housing exterior; and (c) a population of lacrimal epithelial cells within the housing interior. It is understood that a bioartificial lacrimal gland of the invention includes, at a minimum, a single unit and, in some cases, is identical to a unit. In other cases, a bioartificial lacrimal gland of the invention includes two or more units or includes a single unit or a plurality of units held by a unit support in a defined configuration.

As used herein, the term "housing" means any macromolecular structure, carrier or framework which can be formed so as to have an interior within which cells can be contained. A housing may be fabricated from any combination of biological, chemical or other materials which is compatible with implantation into the human eye. Housings useful in the invention include, without limitation, those which are essentially impervious to degradation in the human body as well as those which biodegrade at a variety of rates. Housings useful in the invention further include, without limitation, transparent and opaque housings; non-fouling housings; and housing of varying pliability and tensile strength, including housings with a pliable structure which can accommodate movement within the eye once implanted and which do not create pressure having a detrimental effect on the ocular physiology of the individual receiving the artificial gland.

As used herein, the term "permeable housing" means a structure, either natural or synthetic or a combination thereof, which acts as a highly efficient filter in the range of molecular dimensions, allowing passage of ions, water and other solvents and very small molecules, but almost or entirely preventing passage of macromolecules such as proteins and colloidal particles. A permeable housing generally allows the passage of solvents and small molecules with a diameter of about 8 Å. In one embodiment, a permeable housing useful in the invention has a microporous structure. In another embodiment, a permeable housing useful in the invention is a permeable membrane. One skilled in the art understands that a permeable housing may be constructed from a porous or non-porous biomaterial or a combination thereof.

The term "porous housing," as used herein, means a permeable housing which contains pores. Pores are generally minute cavities in the housing providing a capillary channel to the surface of the housing and can be, for example, substantially linear. Where a porous housing useful in the invention is a porous membrane, such a membrane typically has pores having a diameter of from 8 Å to 100 Å or more. It is understood that a porous housing can be constructed so as to allow directional passage of water and other solvents and small molecules.

Polymers useful in constructing a permeable housing of the invention include, without limitation, non-biodegradable and biodegradable polymers; naturally occurring and synthetic polymers and copolymers; porous and non-porous polymers; linear and branched polymers, homopolymers and copolymers; modified or derivatized polymers and copolymers; polymers and copolymers in which the units have different chiralities; and combinations of two or more of such materials. Polymers and copolymers useful in the invention further include, yet are not limited to, polysiloxanes such as polydimethylsiloxane and copolymers thereof; vinyl polymers and copolymers such as polyvinylpyrrolidone, polymethacrylate and polyvinyl alcohol; acrylic polymers and copolymers; linear and other polyethers such as polyethylene glycol (PEG); polyesters such as poly(glycolic acid), poly (lactic acid) and copolymers of thereof; polypeptides such as collagen; and polysaccharides such as cellulose.

As non-limiting examples, a permeable housing useful in the invention can include a biomaterial such as polysiloxane; polydimethylsiloxane; polyurethane; polyvinylpyrrolidone; polymethacrylate; polyvinyl alcohol; polyethylene; polyethylene glycol; poly(glycolic acid); poly(L-lactic acid); poly (lactic-co-glycolic acid); collagen; cellulose; or a copolymer or derivative thereof. As further non-limiting examples, a permeable housing useful in the invention can include at least 90% of one of the following biomaterials: polysiloxane; polydimethylsiloxane; polyurethane; polyvinylpyrrolidone; polymethacrylate; polyvinyl alcohol; polyethylene; polyethylene glycol; poly(glycolic acid); poly(L-lactic acid); poly(lactic-co-glycolic acid); collagen; cellulose; or a copolymer or derivative thereof.

A permeable housing useful in the invention can be fabricated, for example, from a non-biodegradable biomaterial, which is a biomaterial which does not change substantially over the period of use, for example, one year or five years or longer. In one embodiment, a permeable housing useful in the invention contains a non-biodegradable polymer. In another embodiment, the non-biodegradable polymeric biomaterial is hydrophobic. Non-biodegradable polymeric biomaterials useful in the invention include naturally occurring and synthetic polymeric biomaterials such as, without limitation, polysiloxane; polyurethane; poly(methylmethacrylate); poly (vinyl chloride); poly(ethylene-co-vinyl acetate); polyethylene; and copolymers and derivatives thereof.

As an example, a permeable housing useful in the invention can be fabricated from a non-biodegradable polymeric biomaterial such as polysiloxane, a partially inorganic polymer commonly known as silicone and having the following structure:

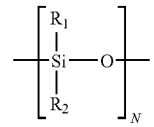

In a particular embodiment, a permeable housing useful in the invention includes the polysiloxane polydimethylsiloxane, also known as PDMS. Polysiloxanes such as PDMS and silicone elastomers, described below, have been useful in biomedical applications, for example, in catheters, drug delivery devices and as tubes which serve as guidance channels for nerve regrowth (Lundborg et al., *J. Neuropath. Exper. Neur.* 41:412-422 (1982)).

Polysiloxanes are chemically inert and stable polymers with excellent biocompatibility, inducing only a limited inflammatory response following implantation. Polysiloxanes also are characterized by high chain flexibility and oxygen permeability, and are stable toward hydrolysis. As is known in the art, the physical characteristics of polysiloxanes can be modified, for example, by varying the polymer molecular weight, degree of cross-linking or by chemical modification, for example, introduction of substituents in place of one or both pendant methyl groups. Polysiloxanes which are cross-linked and those which are reinforced also can be useful in constructing a permeable housing; such polysiloxanes include, without limitation, polysiloxanes reinforced with PET (Dacron) fiber meshes, or polysiloxanes which include cross-linked dimethylsiloxane polymer or silica or both for reinforcement. A permeable housing also can be constructed from a non-biodegradable siloxane copolymer such as, without limitation, dimethylsiloxane copolymerized with ethylene oxide and methyl methacrylate. See, for example, Ulman et al., *J. of Controlled Release* 10:251-260 (1989), Ulman et al., *J. of Controlled Release* 10:261-272 (1989), Ulman and Lee, *J. of Controlled Release* 10:273-281 (1989).

Polysiloxanes can be prepared by routine methods, for example, hydrolysis of alkylsilicon or arylsilicon halides and also are commercially available, for example, from Dow Chemical Corporation. Commercially available polysiloxanes include, without limitation, SILASTIC® products such as the SILASTIC® MDX4-4210 medical grade elastomer. One skilled in the art understands that polysiloxane and other housings constructed of non-porous biomaterials can be permeable or non-permeable, in which case they are generally fabricated in a manner such that pores are introduced.

In a particular embodiment, a permeable housing useful in the invention is a non-porous housing such as a silicone hydrogel similar to those used in extended wear contact lenses. Such silicone hydrogels are well known in the art as described, for example, in Bambury and Seelye, U.S. Pat. No. 5,610,252, and Griesser et al., WO 96/31792.

A permeable housing useful in the invention also can be constructed from polyurethane, a non-biodegradable polymer which has been useful in biomedical applications such as catheters, valves and pacemaker leads. Polyurethanes can be formed by well known methods, for example, reacting a bischloroformate with a diamine as follows:

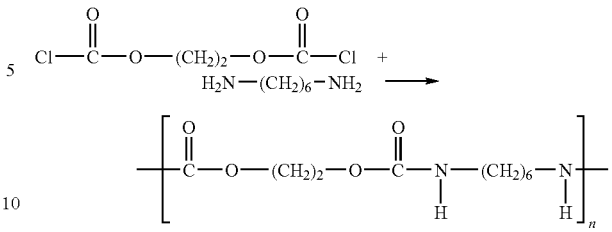

or by reacting a diisocyanate with a dihydroxy compound, for example, ethanediol and hexanediisocyanate, as follows:

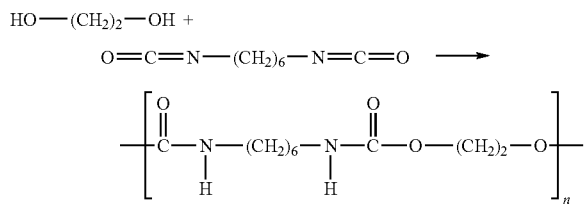

Polyurethane copolymers also can be useful in a permeable housing of the invention; in particular, elastomeric block copolymers containing "hard" and "soft" segments have been useful in biomedical applications. Such polyurethane elastomers can be prepared, for example, by a two-step process in which an aromatic isocyanate-terminated polymer in large excess is reacted with a polyether or polyester containing terminal hydroxyl groups. The product of this reaction is chain extended with a diamine to produce a polymer with urea bonds in addition to urethane linkages. As an example, a segmented polyurethane elastomer can be prepared as follows:

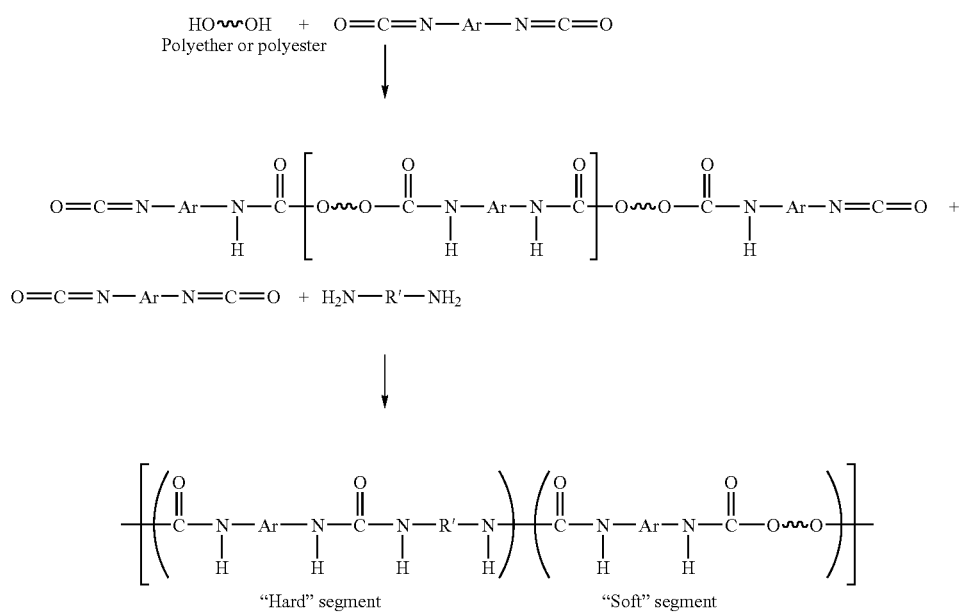

Diisocyanates useful in preparing polyurethane polymers include, without limitation, 4,4'-diphenylmethane diisocyanate (MDI) and 4,4'-dicyclohexylmethane diisocyanate. See Hergenrother et al. *Biomaterials* 14: 449-458 (1993). Chain extenders useful in preparing polyurethane elastomers include, without limitation, diols and diamines. One skilled in the art understands that polyurethanes optionally can be surface-modified, for example, to enhance cell-interaction properties. As a non-limiting example, a polyurethane can be surface modified to add a RGD-containing or other cell adhesion peptide as described in Goodman et al, *J. Biomed. Materials Res.* 27:683-695 (1993), or Lin et al., *J. Biomed. Materials Res.* 28:329-342 (1994).

Polyurethane polymers and copolymers useful in the invention include, without limitation, silicone-urethane copolymers; polycarbonate-urethanes; segmented polyurethanes; aliphatic non-ether based polyurethanes; aromatic ether-based polyurethanes; and aliphatic ether-based polyurethanes (Richards et al., *J. Applied Polymer Sci.* 34:1967-1975 (1987)). A variety of useful polyurethanes are commercially available, for example, ANGIOFLEX® (Abiomed; Danvers, Mass.); BIONATE® (Polymer Technology Group; Berkeley, Calif.); BIOSPAN® (Polymer Technology Group); CARDIOTHANE® (Kontron, Inc.; Everett, Mass.); CHRONOFLEX® (CardioTech International; Woburn, Mass.); ELASTHANE® (Polymer Technology Group); HEMOTHANE® (Sarns; Ann Arbor, Mich.); MITRATHANE® (PolyMedica Corp.; Woburn, Mass.); SURETHANE® (Cardiac Control; Palm Coast, Fla.); and TECOFLEX® (Thermedics; Woburn, Mass.).

A permeable housing useful in the invention also can be constructed from a non-biodegradable vinyl polymer. Vinyl polymers useful in the invention include, but are not limited to, polyvinylpyrrolidone (PVP); polymethacrylate; poly(methyl methacrylate) (pMMA); polyvinyl alcohol (PVA); polyvinyl chloride (PVC); and poly[acrylonitrile-co-(vinyl chloride)]. For example, the vinyl polymer poly(methyl methacrylate) is a biocompatible material previously used in intraocular lenses. Poly(methyl methacrylate), which has the following structure:

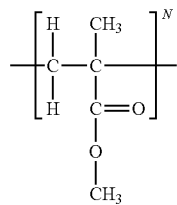

can be routinely prepared using free radical polymerization. Polyvinyl chloride, which has good dimensional stability and chemical resistance, has been used, for example, in medical tubing, catheter tubes and plasmapheresis membranes. Poly [acrylonitrile-co-(vinyl chloride)], which has the structure

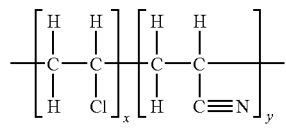

has been used to make semipermeable membranes as well as hollow fibers.

A permeable housing useful in the invention also can be constructed from a copolymer of ethylene and vinyl acetate. Such copolymers, known as polyethylene-co-vinyl acetates or EVAcs, have exceptional biocompatibility and have been widely used in implanted and topical devices including, for example, implantation into rabbit corneas and in OCUSERT® devices (Alzal Mountain View, Calif.) used for drug delivery to the surface of the eye in glaucoma treatment (Langer and Folkman, *Nature* 263:797-800 (1976) and Brown et al., *J. Pharm. Res.* 72:1181-1185 (1983)). Polyethylene-co-vinyl acetates useful in the invention include those which have been washed to remove low molecular weight oligomers and impurities. As a non-limiting example, a poly (ethylene-co-vinyl acetate) copolymer useful in the invention can have 40% vinyl acetate and the general structure

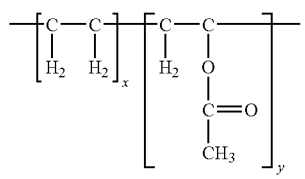

Poly(ethylene-co-vinyl acetate) copolymers can be routinely synthesized, for example, by free radical polymerization from ethylene and vinyl acetate and also are commercially available, for example, from Dupont Corporation, which produces ELVAX® products such as ELVAX®-40, a copolymer containing about 40% vinyl acetate and having a low degree of crystallinity (5-20%). See, for example, Hsu and Langer, *J. Biomed. Materials Res.* 19:445-460 (1985). A permeable housing useful in the invention also can be fabricated from polyethylene-co-vinyl acetate and one or more proteins by, for example, solvent evaporation or compression molding (Siegel and Langer, *Pharmaceutical Research* 2-10 (1984)). Briefly, in solvent evaporation, extensively washed polyethylene-co-vinyl acetate is dissolved in methylene chloride; the one or more proteins are lyophilized, ground and sieved to the desired particle size range, and suspended in the polymer solution. After the suspension is poured into a chilled mold and allowed to solidify, the housing is removed from the mold, dried at atmospheric pressure at −4° C. for 48 hours, and then dried under vacuum at 20° C. for 48 hours.

A non-biodegradable permeable housing useful in the invention also can be constructed from polyethylene, a biocompatible polymer which is inexpensive to produce and easy to process. Polyethylene is well known in the art and has been used in biomedical applications, for example, in catheters (Dumitriu and Dumitriu-Medvichi, *Polymeric Biomaterials*, pp. 3-97, New York: Marcel Dekker, (1994)) and as a guidance channel for nerve regrowth (Madison et al., *Exper. Neurol.* 95:378-390 (1987)).

Biodegradable polymers and other biodegradable materials also can be useful in constructing a permeable housing useful in a bioartificial lacrimal gland of the invention. Biodegradable polymers are those in which the molecular weight of the polymer decreases over time; when the constituent polymeric molecules become sufficiently small, they dissolve, thereby eroding the permeable housing. It is understood that biodegradable polymers may degrade slowly or relatively quickly; as non-limiting examples, a biodegradable polymer or other biomaterial used to construct a permeable housing can have a rate of degradation in the human body of about several weeks to about several years (Kim and Mooney, *Trends Biotech.* 16:224-230 (1998)). One skilled in the art understands that a biodegradable permeable housing can be advantageous in that immunotolerance to the implanted lacrimal epithelial cells can be induced following degradation of the housing. Biodegradable polymers are well known in the art as described, for example, in Saltzman, *Drug Delivery: Engineering Principles for Drug Therapy* New York: Oxford University Press, 2001; and Chasin and Langer (Eds.), *Biodegradable Polymers as Drug Delivery Systems* New York: Marcel Dekker, 1990.

A biodegradable permeable housing useful in the invention can be constructed, for example, from a polyether such as polyethylene glycol (PEG), which has the following structure:

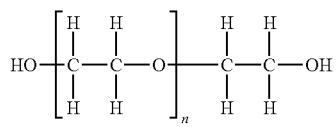

Although low molecular weight PEG (less than 1000 Da) is a liquid at room temperature, higher molecular weight preparations of polyethylene glycol are solids. Furthermore, for use in constructing a permeable housing useful in the invention, a water soluble polymer such as polyethylene glycol also can be crosslinked by chemical or physical means into a solid material or can be prepared in the form of a copolymer. In addition, synthetic RGD-containing or other cell adhesion peptides optionally can be immobilized on a polyethylene glycol permeable housing in order to enhance cell adhesion properties (see, for example, Drumheller et al., *Biotech. Bioengin.* 43:772-780 (1994), and Drumheller and Hubbell, *Anal. Biochem.* 222:380-388 (1994)). Polyethylene glycol is well known in the art for its use in biomedical applications as described, for example, in Harris (Ed.), *Poly(Ethylene Glycol) Chemistry: Biotechnical and Biomedical Applications* New York: Plenum Press, 1992.

A permeable housing useful in the invention also can be fabricated, for example, from a biodegradable polymer such as poly(glycolic acid), poly(L-lactic acid) or poly(lactic-co-glycolic acid). Poly(glycolic acid) and poly(L-lactic acid), which have the following structures

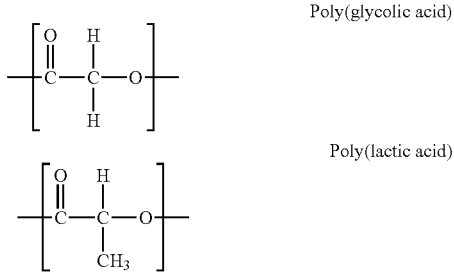

Poly(glycolic acid)

Poly(lactic acid)

and copolymers thereof, are well known in the art as described, for example, in DeLuca et al., *Polymeric Delivery Systems: Properties and Applications* Washington, D.C.: American Chemical Society, pp. 53-79 (1993), and Chasin and Langer (Eds.), *Biodegradable Polymers as Drug Delivery Systems* New York: Marcel Dekker, pp. 1-42 (1990). Poly(glycolic acid) is a widely used synthetic absorbable suture with predictable absorption; outstanding tensile strength; in vivo inertness; excellent handling properties; and high porosity which permits diffusion of nutrients and allows subsequent neovascularization of the developing tissue when used in tissue engineering. Furthermore, poly(glycolic acid) is suitable for preparing permeable housings of varying geometry and provides a surface suitable for cell adherence (Mooney et al., *Biomaterials* 17:115-124 (1996)).

Poly(L-lactic acid), a slowly biodegradable polymer, also can be useful in preparing a permeable housing useful in the invention. Poly(L-lactic acid) is known in the art as a material suitable for tissue engineering as described, for example, in Aframian et al., *Tissue Engineering* 6:209-216 (2000). As compared to poly(glycolic acid), poly(L-lactic acid) degrades more slowly and has greater resistance to compressional forces. Advanced polymer processing technology can furnish, for example, fibers and sheets of poly(L-lactic acid) with high tensile strength and high transparency (see, for example, Tsuji et al., *Curr. Interv. Cardiol. Rep.* 3:10-17 (2001); Langer and Vicanti, *Science* 260: 920-926 (1993); and Aframian et al., supra, 2000).

Copolymers of lactic and glycolic acid also can be useful in fabricating a permeable housing useful in a bioartificial lacrimal gland of the invention. Such biodegradable polymers, for example, 50/50 and 85/15 copolymers of lactic acid and glycolic acid, are well known in the art of tissue engineering (Aframian et al., supra, 2000). These porous, biodegradable copolymers can be prepared by well-known methods including, without limitation, the gas foaming polymer processing approach described in Sheridan et al., *J. Controlled Release* 64:91-102 (2000).

The biodegradable polymer collagen, which has been used in preparation of a variety of ophthalmic devices and drug delivery platforms, also can be useful in fabricating a permeable housing for use in a bioartificial lacrimal gland of the invention. Collagens are abundant proteins which in nature are secreted into the extracellular space by chondrocytes, fibroblasts and other cell types. Collagens useful in the invention include, without limitation, collagens type I, type II, type III and type IV. Collagens are structurally characterized as an alpha-helical chain formed by three polypeptides of about 1000 amino acids which are specific to each type of collagen. Collagen types I, II and III generally organize into larger fibrils of about 10 to 300 nm in diameter which are stabilized by crosslinking between lysine residues. Unlike the fibrillar collagens, collagen type IV forms a mesh-like lattice that in nature constitutes a major part of the mature basal lamina.

A permeable housing useful in the invention also can include a naturally occurring, biodegradable polymer such as a polysaccharide. As an example, the polysaccharide cellulose, and derivatives thereof, have previously been useful as dialysis membranes. In one embodiment, a permeable housing useful in the invention is fabricated from cellulose, which is a polymer of glucose residues connected by β-(1,4) linkages

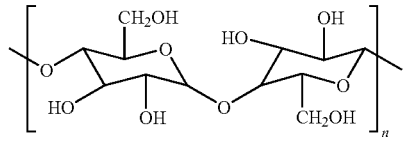

A permeable housing useful in the invention also can be prepared using a biodegradable synthetic polymer such as a poly(anhydride), poly(orthoester) or another synthetic polymer having functional groups available for covalent modification (Peppas and Langer, *Science* 263:1715-1720 (1994)).

Amino-acid-based polymers also can be useful for fabrication of a permeable housing including, without limitation, artificial collagen-like, silk-like and elastin-like proteins expressed in bacteria (James and Kohn, *MRS Bull.* 21:22-26 (1996)); such amino-acid-based polymers can advantageously interact with cells. Chemically synthesized pseudo-poly(amino acid)s, such as tyrosine-derived polycarbonates or polyarylates, also can be useful in fabricating a porous housing useful in the invention (James and Kohn, supra, 1996). One skilled in the art understands that a porous housing composed of a biomaterial with a hydrophobic surface can promote cell adhesion through a hydrophobic interaction with the lacrimal epithelial cell membrane. Biomaterials with a hydrophobic surface include, but are not limited to, plastics and other polymers to which hydrophobic groups have been linked, for example, polystyrene, polyethylene and polyvinyl. One skilled in the art understands that these and a variety of other well known naturally occurring and synthetic non-biodegradable and biodegradable biomaterials can be useful in constructing a permeable housing useful in the invention. See, for example, Lewandrwoski et al. (Eds.), *Scientific and Clinical Applications* New York: M. Dekker (2002); Saltzman, *Tissue Engineering: Engineering Principles for the Design of Replacement Organs and Tissues* New York: Oxford University Press (2004); Palsson and Sangeeta, *Tissue Engineering* New Jersey: Pearson Prentice Hall (2004); and Guilak et al., *Functional Tissue Engineering* New York: Springer (2003).

A permeable housing useful in the invention can have any of a variety of shapes and sizes, which typically are chosen to promote, for example, the native in situ cytoskeletal organization, tight junction formation, polarization or monolayer formation of the population of lacrimal epithelial cells within the housing interior. In particular embodiments, the permeable housing has a concave interior surface such as a substantially cylindrical interior surface or a substantially spherical interior surface. In a further embodiment, the permeable housing is substantially tubular; such a permeable housing can be a tube such as a tube having a first closed end and a second end which is the outlet connecting the housing interior to the housing exterior. Where the permeable housing of a bioartificial lacrimal gland is tubular, the tube can have a lumen, for example, of uniform diameter. In particular embodiments, the lumen of the tube has a diameter of no more than 2 mm or a diameter of between 0.1 and 0.5 mm. In further embodiments, the length of the tube is at most 10 mm or at most 5 mm. As discussed further below, a permeable housing useful in the invention can be a porous housing having any of a variety of pore sizes including, without limitation, a pore size of between 0.01 and 10 microns or a pore size of between 0.1 and 5 microns.

As used herein in reference to a permeable housing, the term "substantially tubular" means a hollow body having a concave interior surface and an axial length which is significantly longer than either the width or depth of the permeable housing. As non-limiting examples, the axial length can be at least two, three, four, five, six, seven, eight, nine, ten, eleven, twelve, thirteen, fourteen, fifteen, sixteen, seventeen, eighteen, nineteen, twenty, thirty, forty or fifty times the greater of the width or depth of the permeable housing. Where the permeable housing is cylindrical, the axial length can be, without limitation, at least two, three, four, five, six, seven, eight, nine, ten, eleven, twelve, thirteen, fourteen, fifteen, sixteen, seventeen, eighteen, nineteen, twenty, thirty, forty or fifty times the diameter of the cylinder. It is understood that, while a substantially tubular permeable housing has a concave interior surface, the exterior of a substantially tubular permeable housing may have a variety of shapes and will not necessarily be convex.

The lumen of a substantially tubular permeable housing can be, for example, symmetrical or non-symmetrical and further can be, without limitation, cylindrical, elliptical or oblong. It is understood that the lumen of a substantially tubular permeable housing can have a regular or irregular diameter such as, without limitation, a fixed diameter, a diameter which periodically increases and decreases, or a tapering diameter which is narrower at one end than the other. In one embodiment, a substantially tubular permeable housing has a first closed end and a second end which is an outlet connecting the housing interior to the housing exterior. The outlet can be, for example, narrower, wider or roughly the same dimension as the closed end of the substantially tubular permeable housing. In another embodiment, the substantially tubular permeable housing is a tube. As used herein, the term "tube" means a hollow body with parallel sides and a concave interior surface. A tube can have, for example, a circular or elliptical cross section and can be, without limitation, a cylinder. As used herein, the term "cylinder" means a uniform hollow body with parallel sides and a circular cross-section.

A permeable housing useful in a bioartificial lacrimal gland of the invention can be constructed with any of a variety of dimensions. In general, a permeable housing useful in the invention has an axial length of at most 20 mm and an inner diameter of at most 3 mm. Such a permeable housing can have, for example, an axial length of at most 20 mm, 18 mm, 15 mm; 14 mm; 13 mm; 12 mm; 11 mm; 10 mm; 9 mm; 8 mm; 7 mm; 6 mm; 5 mm; 4 mm; 3 mm; 2 mm or 1 mm. As non-limiting examples, a permeable housing useful in the invention can have, for example, an axial length of from 1 mm to 15 mm; 1 mm to 12 mm; 1 mm to 10 mm; 1 mm to 8 mm; 1 mm to 6 mm; 1 mm to 5 mm; 1 mm to 4 mm; 1 mm to 3 mm; 3 mm to 15 mm; 3 mm to 12 mm; 3 mm to 10 mm; 3 mm to 8 mm; 3 mm to 6 mm; 3 mm to 5 mm; 4 mm to 15 mm; 4 mm to 12 mm; 4 mm to 10 mm; 4 mm to 8 mm; 4 mm to 6 mm; 5 mm to 15 mm; 5 mm to 12 mm; 5 mm to 10 mm; 5 mm to 8 mm; 5 mm to 6 mm; 6 mm to 15 mm; 6 mm to 12 mm; 6 mm to 10 mm; or 6 mm to 8 mm.

A permeable housing useful in the invention also can have, for example, an inner diameter of at most 3.00 mm; 2.75 mm; 2.50 mm; 2.25 mm; 2.00 mm; 1.90 mm; 1.80 mm; 1.70 mm; 1.60 mm; 1.50 mm; 1.40 mm; 1.30 mm; 1.20 mm; 1.10 mm; 1.00 mm; 0.95 mm; 0.90 mm; 0.85 mm; 0.80 mm; 0.75 mm; 0.70 mm; 0.65 mm; 0.60 mm; 0.55 mm; 0.50 mm; 0.45 mm; 0.40 mm; 0.35 mm; 0.30 mm; 0.25 mm; 0.20 mm; 0.15 mm; 0.10 mm or 0.05 mm. A permeable housing useful in the invention also can have, for example, an inner diameter of at least 0.05 mm; 0.10 mm; 0.15 mm; 0.20 mm; 0.25 mm; 0.30 mm; 0.35 mm; 0.40 mm; 0.45 mm; 0.50 mm; 0.55 mm; 0.60 mm; 0.65 mm; 0.70 mm; 0.75 mm; 0.80 mm; 0.85 mm; 0.90 mm; 0.95 mm; 1.00 mm; 1.10 mm; 1.20 mm; 1.30 mm; 1.40 mm; 1.50 mm; 1.60 mm; 1.70 mm; 1.80 mm; 1.90 mm; 2.00 mm; 2.25 mm; 2.50 mm; 2.75 mm; or 3.00 mm. As non-limiting examples, a permeable housing useful in the invention can have, for example, an inner diameter of from 0.05 mm to 2 mm; 0.05 mm to 1.5 mm; 0.05 mm to 1.25 mm; 0.05 mm to 1.0 mm; 0.05 mm to 0.90 mm; 0.05 mm to 0.8 mm; 0.05 mm to 0.7 mm; 0.05 mm to 0.6 mm; 0.05 mm to 0.5 mm; 0.05 mm to 0.4 mm; 0.05 mm to 0.3 mm; 0.05 mm to 0.2 mm; 0.1 mm to 2 mm; 0.1 mm to 1.5 mm; 0.1 mm to 1.25 mm; 0.1 mm to 1.0 mm; 0.1 mm to 0.90 mm; 0.1 mm to 0.8 mm; 0.1 mm to 0.7 mm; 0.1 mm to 0.6 mm; 0.1 mm to 0.5 mm; 0.1 mm to 0.4 mm; 0.1 mm to 0.3 mm; 0.1 mm to 0.2 mm; 0.2 mm to 2 mm; 0.2 mm to 1.5 mm; 0.2 mm to 1.25 mm; 0.2 mm to 1.0 mm; 0.2 mm to 0.90 mm; 0.2 mm to 0.8 mm; 0.2 mm to 0.7 mm; 0.2 mm to 0.6 mm; 0.2 mm to 0.5 mm; 0.2 mm to 0.4 mm; 0.2 mm to 0.3 mm; 0.3 mm to 2 mm; 0.3 mm to 1.5 mm; 0.3 mm to 1.25 mm; 0.3 mm to 1.0 mm; 0.3 mm to 0.90 mm; 0.3 mm to 0.8 mm; 0.3 mm to 0.7 mm; 0.3 mm to 0.6 mm; 0.3 mm to 0.5 mm; 0.3 mm to 0.4 mm; 0.4 mm to 2 mm; 0.4 mm to 1.5 mm; 0.4 mm to 1.25 mm; 0.4 mm to 1.0 mm; 0.4 mm to 0.90 mm; 0.4 mm to 0.8 mm; 0.4 mm to 0.7 mm; 0.4 mm to 0.6 mm; 0.4 mm to 0.5 mm; 0.5 mm to 2 mm; 0.5 mm to 1.5 mm; 0.5 mm to 1.25 mm; 0.5 mm to 1.0 mm; 0.5 mm to 0.90 mm; 0.5 mm to 0.8 mm; 0.5 mm to 0.7 mm; or 0.5 mm to 0.6 mm.

In particular embodiments, a permeable housing useful in the invention has an axial length of from 3 mm to 12 mm and an inner diameter of from 0.05 to 0.6 mm, 0.1 to 0.5 mm, 0.2 to 0.4 mm, 0.25 to 0.35 mm or about 0.3 mm. In further embodiments, a permeable housing useful in the invention has an axial length of from 3 mm to 10 mm and an inner diameter of from 0.05 to 0.6 mm, 0.1 to 0.5 mm, 0.2 to 0.4 mm, 0.25 to 0.35 mm or about 0.3 mm. In additional embodiments, a porous housing useful in the invention has an axial length of from 3 mm to 8 mm and an inner diameter of from 0.05 to 0.6 mm, 0.1 to 0.5 mm, 0.2 to 0.4 mm, 0.25 to 0.35 mm or about 0.3 mm. In still further embodiments, a permeable housing useful in the invention has an axial length of from 4 mm to 6 mm and an inner diameter of from 0.05 to 0.6 mm, 0.1 to 0.5 mm, 0.2 to 0.4 mm, 0.25 to 0.35 mm or about 0.3 mm.

A permeable housing useful in the invention also can have any of a variety of thicknesses from about 0.01 mm to 1 mm, for example, from 0.01 mm to 0.5 mm or from 0.05 mm to 0.5 mm. As non-limiting examples, the thickness of the permeable housing can be at most 0.1 mm; 0.2 mm; 0.3 mm; 0.4 mm; 0.5 mm; 0.6 mm; 0.7 mm; 0.8 mm; 0.9 mm or 1.0 mm. As further non-limiting examples, the thickness of the permeable housing can be at least 0.01 mm; 0.025 mm; 0.050 mm; 0.075 mm; 0.1 mm; 0.2 mm; 0.3 mm; 0.4 mm; or 0.5 mm. It is understood that the dimensions of a permeable housing can be varied by the skilled person and that permeable housings of these and other dimensions can be useful in the bioartificial glands of the invention.

In selecting the size and shape of a permeable housing, it is understood that one skilled in the art will take into consideration the ocular anatomy of the individual into whom the bioartificial lacrimal gland is being implanted including, for example, the curvature of the individual's eye and the etiology of the lacrimal gland dysfunction. One skilled in the art further will take into consideration the extent of lacrimal gland dysfunction including the extent of residual lacrimal gland function, if any.

In one embodiment, a permeable housing useful in the invention is a porous housing. In another embodiment, a permeable housing useful in the invention is a porous membrane. As used herein, the term "membrane" means a thin, pliable sheet of material. In general, a porous membrane has a thickness of at most 0.25 mm, for example, from 0.03 to 0.2 mm or from 0.03 to 0.1 mm and, further, typically has an effective water permeation rate of at least $0.18 \times 10^{-6}$ cm$^2$/second. Porous membranes useful in the invention can have, for example, a pliability similar to that of a soft contact lense and include, without limitation, those made of synthetic materials such as synthetic polymers; film membranes such as silicone film membranes; and symmetric and asymmetric porous membranes. Thus, porous membranes useful in the invention include, without limitation, asymmetric membranes, which possess a thin layer for size selectivity and a thicker, more porous layer for mechanical strength, and further include asymmetric membranes like ones used in separation processes such as dialysis.

As non-limiting examples, membrane polymers which have been used in hemodialysis and hollow fiber bioreactors can be useful in fabricating a permeable housing which is a porous membrane; such membrane polymers include, but are not limited to, cellulose and derivatives thereof such as cellulose diacetate, cellulose triacetate and diethylaminoethyl-substituted cellulose; polymethylmethacrylate; poly(acrylonitrile-co-vinyl chloride); polyacrylonitrile-methacrylate copolymer; polyacrylonitrile-methallyl sulfonate copolymer; and polysulfone (see, for example, Pastan and Bailey, *New Engl. J. Med.* 338: 1428-1437 (1998)). Porous membranes useful in the invention further include silicone hydrogels and other membranes of a biphasic nature. In particular, a porous membrane useful in the invention can be a biphasic silicone hydrogel such as, without limitation, a perfluoroalkylether macromer with two polymerizable groups; a polysiloxane-containing perfluoroalkylether; a polymerizable perfluoroalkylether siloxane macromer or a polymerizable perfluoroalkylether macromer.

A bioartificial lacrimal gland of the invention also includes an outlet connecting the housing interior to the housing exterior. As used herein, the term "outlet" means an opening in the permeable housing through which water and solutes can pass but which does not permit release of lacrimal epithelial cells from the housing interior. It is understood that an outlet can have a variety of positions on the permeable housing. For example, where the permeable housing is a tube or other substantially tubular structure, the outlet can be positioned anywhere along the length of the tube or at one end of the tube and that the outlet is significantly longer than the pores of a porous housing.

A variety of lacrimal epithelial cell populations can be useful in a bioartificial lacrimal gland of the invention. As described above, the lacrimal epithelial cells can be polarized and, further, can be arrayed in a polarized monolayer. Such a polarized monolayer of lacrimal epithelial cells optionally can be adhered to a viscous substratum. Any of a variety of lacrimal epithelial cells are useful in the bioartificial lacrimal glands of the invention including, without limitation, primary cells, established cells, transfected cells, and cells from a variety of species. In one embodiment, the population of lacrimal epithelial cells is a population of human lacrimal epithelial cells. In another embodiment, the population of lacrimal epithelial cells is a population of rabbit lacrimal epithelial cells.

Cell populations useful in the invention include those in which the cell population within the housing interior is at least 80% pure lacrimal epithelial cells. In another embodiment, the cell population within the housing interior is at least 90% pure lacrimal epithelial cells. In still another embodiment, the cell population within the housing interior is at least 95% pure lacrimal epithelial cells. In further embodiments, the cell population within the housing interior is at least 96%, 97%, 98% or 99% pure lacrimal epithelial cells.

Lacrimal epithelial cells useful in the invention include, without limitation, naturally occurring and genetically engineered cells, and further encompass primary cells including primary cells which have been expanded in culture; lacrimal epithelial cells from established cell lines; immortalized; transfected and infected cells; and live and attenuated cells. Lacrimal epithelial cells useful in the invention can be immortalized primary patient cells or immortalized primary cells from a close relative of the patient. Immortalized lacrimal gland cell lines also are useful in the invention and encompass immortalized rabbit cell lines such as those described in Nguyen et al., *In Vitro Cell Dev. Biol. Anim.* 35:198-204 (1999), and Saarloos et al., *Curr. Eye Res.* 19:439-449 (1999). Lacrimal epithelial cells also can be prepared, for example, by differentiating stem cells in vitro or in vivo. Lacrimal epithelial cells useful in the invention include, but are not limited to, mammalian cells such as human cells; cells from higher order mammals such as primates, dogs and cats; rabbit cells and goose cells. One skilled in the art understands that these and other species of lacrimal epithelial cells can be useful in a bioartificial lacrimal gland to be implanted into a human patient. Such lacrimal epithelial cells can be characterized, for example, by containing enzymes similar to those generally found in human lacrimal epithelial cells.

Lacrimal epithelial cells useful in the invention further include those which express an exogenous nucleic acid molecule. As is well known in the art, primary or immortalized lacrimal epithelial cells can be transfected or infected, for example, and thereby express an exogenous nucleic acid molecule. Methods for gene delivery into lacrimal epithelial cells include, without limitation, the use of adenoviral or vaccinia viral vectors such as Ad5CMV or VSC9 as described, for example, in Vanaken et al., *J. Steroid Biochem. Mol. Biol.* 78:319-328 (2001), and Banin et al., *Invest. Ophthalmol. Vis. Sci.* 44:1529-1533 (2003). Exogenous nucleic acid molecules which can be expressed in lacrimal epithelial cells for use in a bioartificial gland of the invention include, without limitation, receptors; integrins; growth factors such as epidermal growth factor; pro-angiogenic agents such as fibroblast growth factor (FGF) or vascular endothelial growth factor (VEGF); extracellular matrix molecules; and transport proteins including, but not limited to, those described in Baum et al., supra, 1993.

In the methods of the invention for treating or reducing the severity of a disorder of lacrimal gland dysfunction, the lacrimal epithelial cells can be autologous, allogeneic or xenogeneic with respect to the individual into whom the bioartificial lacrimal gland is implanted. Autologous lacrimal epithelial cells are those derived from the same individual into whom the bioartificial gland is implanted. Allogenic lacrimal epithelial cells are those derived from a genetically different individual of the same species as the individual into whom the bioartificial gland is implanted, and xenogenic lacrimal epithelial cells are those derived from an individual of a different species as the individual into whom the bioartificial gland is implanted. For treatment of humans, allogeneic cells may be derived, for example, from a family member or a non-family member and can be HLA matched cells or unmatched cells. By HLA matched cells, it is meant that one or more of the major histocompatibility complex (MHC) molecules on the lacrimal epithelial cells included in the bioartificial gland is the same as one or more of the MHC molecules on the cells of the individual into whom the bioartificial gland is implanted. Such HLA matched allogeneic cells include, yet are not limited to, HLA-A2 matched cells. One skilled in the art understands that unmatched allogenic lacrimal epithelial cells can be rendered immunocompatible, for example, by genetic engineering to alter cell surface expression of one or more antigens. Matched or unmatched allogeneic cells also can be used in conjunction with an immunosuppressive agent as described further below.

A bioartificial lacrimal gland of the invention optionally includes a viscous substratum within the housing interior. The term "viscous substratum," as used herein, means a viscous organic or inorganic material which promotes the growth, attachment, polarization or tight junction formation of lacrimal epithelial cells. A viscous substratum can promote, for example, formation of a monolayer of polarized lacrimal epithelial cells. In one embodiment, the viscous substratum is adhered to the interior surface of the permeable housing. In another embodiment, the bioartificial lacrimal gland is constructed such that the viscous substratum adheres to the interior surface of the permeable housing, and the polarized monolayer of lacrimal epithelial cells adheres to the viscous substratum.

A viscous substratum useful in the invention generally has a tensile strength which is significantly lower than the tensile strength of the permeable housing in which it resides. The term tensile strength is well known in the art and means the resistance of a material to a force such as a longitudinal force tending to tear it apart, measured as the maximum tension the material can withstand without tearing. In one embodiment, a viscous substratum useful in the invention has a tensile strength which is at most 50% of the tensile strength of the permeable housing in which it resides. In further embodiments, a viscous substratum useful in the invention has a tensile strength which is at most 45%, 40%, 35%, 30%, 25%, 20%, 15% or 10% of the tensile strength of permeable housing in which it resides. One skilled in the art understands that tensile strength can be varied by the skilled artisan and is a property which generally depends upon the component biomaterial or biomaterials of the permeable housing or viscous substratum as well as the extent of cross-linking and extent and type of modification, if any, of the housing and substratum.

A viscous substratum useful in the invention can be a gel such as a hydrogel. As used herein, the term "gel" is synonymous with "colloidal gel" and means a mixture with properties between those of a solution and fine suspension which is in a more solid form than a sol. The term "hydrogel," as used herein, means a colloidal gel in which water is the dispersion medium.

A viscous substratum useful in the invention can be a simple or complex material and further can be porous or non-porous. Viscous substrata useful in the invention include, without limitation, those containing one or more naturally occurring or synthetic components such as, without limitation, a peptide, protein, polysaccharide or other polymeric component. As non-limiting examples, a viscous substratum useful in the invention can include a protein such as an extracellular matrix component, gelatin or poly-lysine. As further non-limiting examples, a viscous substratum useful in the invention can include collagen, hydroxymethylcellulose, hyaluronan, or a copolymer or derivative thereof As additional non-limiting examples, a viscous substratum useful in the invention can include a polysaccharide such as, without limitation, cellulose; starch; glycogen; chitosane; or animated sepharose. One skilled in the art understands that these and other viscous substrata including, without limitation, those which function to provide a porous layer for adherence of lacrimal epithelial cells and those which function to promote the growth or polarization of lacrimal epithelial cells, can be useful in the bioartificial lacrimal glands of the invention.

Extracellular matrix components which can be included in a viscous substratum of the invention encompass, without limitation, MATRIGEL™; vitrogen; fibronectin; laminin; and collagens such as collagen type I or collagen type IV. In one embodiment, a viscous substratum useful in the invention includes MATRIGEL™, which is a well known solubilized preparation made from basement membranes isolated from the EHS mouse sarcoma line, a tumor cell line rich in extracellular matrix molecules. MATRIGEL™ includes substantial amounts of laminin, collagen IV, heparan-sulfate proteoglycans, entactin and nidogen (Kleinman et al., *Biochem.*

21:6188-6193 (1982)) and contains transforming growth factor (TGF-β), basic fibroblast growth factor-2 (FGF-2), tissue plasminogen activator (TPA) and other growth factors. When included in a viscous substratum, MATRIGEL™ typically is present at a final concentration of about 0.01 mg/ml to 100 mg/ml, for example, 0.1 mg/ml to 20 mg/ml, 0.1 mg/ml to 10 mg/ml, 0.1 mg/ml to 5 mg/ml, 0.1 mg/ml to 2.5 mg/ml, 0.1 mg/ml to 1.0 mg/ml, 0.25 mg/ml to 10 mg/ml, 0.25 mg/ml to 5 mg/ml, 0.25 mg/ml to 2.5 mg/ml or 0.25 mg/ml to 1.0 mg/ml. In a particular embodiment, a bioartificial gland of the invention includes a viscous substratum in which MATRIGEL™ is present at a final concentration of 0.25 to 5 mg/ml. In a further embodiment, a bioartificial gland of the invention includes a viscous substratum containing fetal bovine serum in addition to MATRIGEL™ at a final concentration of 0.25 to 5 mg/ml. Techniques for applying MATRIGEL™ to a permeable housing during construction of a bioartificial lacrimal gland of the invention are described herein below.

A bioartificial lacrimal gland of the invention includes at least one unit which contains (a) a permeable housing having an interior and an exterior; (b) an outlet connecting the housing interior to the housing exterior; and (c) a population of lacrimal epithelial cells within the housing interior. In particular embodiments, a bioartificial lacrimal gland of the invention includes a plurality of such units, for example, at least three units or at least five units. In further embodiments, a bioartificial lacrimal gland of the invention additionally includes a unit support which holds each of the plurality of units in a defined configuration, for example, a unit support which holds each of the plurality of units substantially in parallel. Any of the above bioartificial lacrimal glands of the invention including a plurality of units may optionally include an encapsulating membrane which is impermeable to antibodies and immune cells.

In a bioartificial lacrimal gland of the invention including a plurality of units, the permeable housing can be, without limitation, a tube, and additionally can be a tube having a first closed end and a second end which is the outlet connecting the housing interior to the housing exterior. Furthermore, in a bioartificial lacrimal gland of the invention including a plurality of tubes having first closed ends and second ends which are outlets, the gland may optionally include a common duct which is joined to each of the outlets. In one embodiment, the common duct further includes a gate which is optionally responsive to a stimulus. In another embodiment, a bioartificial lacrimal gland of the invention includes an encapsulating membrane which is impermeable to antibodies and immune cells. As a non-limiting example, a bioartificial lacrimal gland containing three units based on a porous tubular housing is shown in FIG. 2.

A bioartificial lacrimal gland having a plurality of units can be advantageous as compared to a bioartificial gland having a single unit since the gland with a plurality of units can produce a greater directional fluid secretion rate while maintaining a limited radius of curvature of the concave interior surface and a limited axial length of the individual units. As non-limiting examples, a bioartificial lacrimal gland including a plurality of units can have at least two, three, four, five, six, seven, eight, nine, ten, eleven, twelve, thirteen, fourteen, fifteen, sixteen, seventeen, eighteen, nineteen, twenty, thirty, forty, fifty, sixty, seventy, eighty, ninety, 100, 200, or more units, which units can be identical or non-identical. One skilled in the art understands that the number of units will be selected taking in account the ocular anatomy of the individual into whom the gland is being implanted; the severity of lacrimal gland dysfunction including the extent of residual lacrimal gland function, if any; and the desired fluid-secretion rate.

The optional unit support can have, for example, a top side, which faces away from the eye and a bottom side, which is in direct or indirect contact with the globe of the eye. In a bioartificial lacrimal gland of the invention, it is the top side of the unit support which typically directly or indirectly holds the plurality of units in a defined configuration. Furthermore, in a bioartificial lacrimal gland of the invention, the bottom of the unit support typically is shaped to fit the contour of the globe such that the unit support arches over the globe.

The size and dimensions of a bioartificial lacrimal gland including the plurality of units and the unit support, if any, can vary. In general, a bioartificial lacrimal gland of the invention has a length of at most 30 mm; a width of at most 30 mm and a depth of at most 5 mm. As non-limiting examples, a bioartificial lacrimal gland of the invention, including any number of units and optionally a unit support can have, without limitation, a length of from 1 mm to 20 mm, a width of from 1 mm to 20 mm and a depth of from 0.5 to 5 mm, or a length of from 1 mm to 10 mm, a width of from 1 mm to 10 mm; and a depth of from 0.5 to 5 mm. One skilled in the art understands that these are illustrative dimensions which can be varied by one skilled in the art of ophthalmology.

A bioartificial lacrimal gland of the invention can be made by routine methods. The bioartificial gland can include an integrally formed permeable housing or a housing constructed from two or more components or surface treatments. The permeable housing can be manufactured as a unitary or multi-component structure in a variety of ways as will be appreciated by those of skill in the art. In one embodiment, the permeable housing includes at least two components connected together. For example, where the unit gland includes an attachment surface on the exterior surface of the permeable housing to aid in tissue ingrowth, an outer sleeve of porous material such as expanded polytetrafluoroethylene (PTFE) or other tissue ingrowth material can be attached by bonding the two components together using, without limitation, solvent bonding, thermal bonding, adhesives or other means well known in the art.

A variety of well known techniques are suitable for preparing a permeable housing from a polymeric or non-polymeric biomaterial. Such techniques include, yet are not limited to, gas foaming polymer processing methods; solvent evaporation methods; phase separation methods; interfacial methods; extrusion methods; molding methods including injection molding methods; heat press methods and the like. See U.S. Pat. Nos. 5,164,188 and 5,660,847 and Scott and Roff (Eds.), *Handbook of Common Polymers* Section 64; CRC Press; Cleveland, Ohio (1971). As a non-limiting example, a poly(glycolic acid); poly(lactic acid); or poly(lactic-co-glycolic acid) polymer can be fabricated into the desired shape of porous permeable housing using a well known technique such as molding, extrusion or solvent casting (Kim and Mooney, supra, 1998). As further non-limiting examples, a permeable housing can fabricated using injection molding, which is well known in the art as described, for example, in U.S. Pat. Nos. 3,432,592; 4,801,460; 4,806,377; 5,004,601; 5,082,655; and 6,331,313, or can be fabricated using gas foaming polymer processing with $CO_2$ and biomaterials such as, without limitation, amorphous copolymers of lactide and glycolide without organic solvents or high temperatures essentially as described in Sheridan et al., supra, 2000. As described further below, a pro-angiogenic agent or other component can be incorporated into the permeable housing during the fabrication process, for example, for subsequent controlled release (Sheridan et al., supra, 2000).

As a non-limiting example, a tubular permeable housing with a viscous substratum including MATRIGEL™ can be prepared essentially as follows. MATRIGEL™, which is soluble at 4° but forms a gel at 37°, can be thawed overnight on ice in a refrigerator and, immediately before use, diluted into cold HEPATO STIM® Culture Medium (HSM) containing 10% fetal bovine serum (FBS; Omega Scientific, Inc.; Tarzana, Calif.) and 5 ng/ml epidermal growth factor (EGF). The final working concentration of MATRIGEL™ for use in applying the viscous substratum to the tubular permeable housing is approximately 1 mg/ml. The solution of MATRIGEL™ can be applied, for example, into a doubly open-ended tubular permeable housing essentially as follows. The doubly open-ended permeable housing is perfused at 4° with a solution of diluted MATRIGEL™ in HEPATO STIM® Culture Medium and subsequently briefly perfused with media that does not contain MATRIGEL™. The unstirred fluid layer adjacent to the interior surface of the tubular permeable housing contains the MATRIGEL™ solution. Upon transfer of the tubular permeable housing to a 37° water bath, MATRIGEL™ lines the interior wall of tubular housing while the lumen of the permeable housing remains patent. One skilled in the art can vary, for example, the MATRIGEL™ concentration, length of the tubular permeable housing, and perfusion rate in order to obtain a viscous substratum which is suitably uniform. If desired, one skilled in the art can readily section the tubular housing for evaluation of the thickness and uniformity of the viscous substratum by microscopy.

A population of lacrimal epithelial cells can subsequently be applied into the interior of the MATRIGEL™-lined tubular permeable housing essentially as follows. In particular, a suspension of lacrimal epithelial cells is perfused through permeable housing; such a cell population can be, for example, suspended in HEPATO STIM® Culture Medium (HSM) and perfused at 37° C. or, for example, suspended in dilute MATRIGEL™ and perfused at 4° C., then warmed to 37° C. One skilled in the art can routinely vary parameters such as the cell concentration, perfusion rate and MATRIGEL™ concentration, if any, as well as the length of the tubular housing and the lumen diameter to achieve the desired characteristics such as lacrimal cell polarization, monolayer formation and tight junction formation. The concentration of cells which is perfused generally is in the range of $1 \times 10^6$ cells/ml to $5 \times 10^7$ cells/ml, and can be, for example, in the range of $5 \times 10^6$ cells/ml to $1 \times 10^7$ cells/ml or $2 \times 10^7$ cells/ml to $4 \times 10^7$ cells/ml Perfusion rates typically are in the range of 0.1 ml/minute to 5 ml/minute, and can be, for example, in the range of 0.1 ml/minute to 3 ml/minute or 0.5 ml/minute to 5 ml/minute. When included in the cell suspension, MATRIGEL™ generally is provided at a concentration of from 0.3 mg/ml to 5 mg/ml, for example, from 1 mg/ml to 3 mg/ml, or from 0.5 mg/ml to 2 mg/ml.

Further provided herein is a method of treating or reducing the severity of a disorder resulting from lacrimal gland dysfunction in an individual by implanting into the individual a bioartificial lacrimal gland which includes at least one unit containing (a) a permeable housing having an interior and an exterior; (b) an outlet connecting the housing interior to the housing exterior; and (c) a population of lacrimal epithelial cells within the housing interior.

The methods of the invention can be useful for treating or reducing the severity of any of a variety of disorders resulting from lacrimal gland dysfunction including disorders of any etiology. One skilled in the art understands that disorders to be treated by a method of the invention may result from a reduction in either the quality or quantity of fluid which forms the tear film of the ocular surface and may be, for example, disorders of partial or complete lacrimal gland hypofunction or disorders in which the tear ducts are blocked. Disorders of lacrimal gland dysfunction which can be treated or reduced in severity according to a method of the invention encompass, but are not limited to, Stevens-Johnson syndrome; chemical and thermal eye injuries; ocular cicatricial pemphigoid; Sjögren's syndrome; rheumatoid arthritis; lupus; and dry eye syndrome of a variety of etiologies.

In one embodiment, a method of the invention is used to treat dry eye syndrome (keratoconjunctivitis), which is an inflammation of the cornea and conjunctiva due to the normal aging of the tear glands or to one of a number of specific pathologies. See, for example, Tsubota, *Adv. Exp. Med. Biol.* 506 (Part A): 3-16 (2002); Schaumberg et al., *Adv. Exp. Med. Biol.* 506 (Part B): 989-998 (2002); and Johnson and Murphy, *Prog. Retin. Eye Res.* 23(4):449-474 (2004). Dry eye syndrome generally is characterized by hyperemia of the conjunctiva, lacrimal deficiency, thickening of the corneal epithelium, itching and burning of the eye and, often, reduced visual acuity. In dry eye syndrome, the decline in the quality or quantity of fluid that forms the tear film of the ocular surface results in constant discomfort from eye irritation which is typically experienced as a sandy or gritty sensation. In the early stages of the disorder, the symptoms of dry eye may be intermittent, but generally become more persistent as dry eye continues. When untreated, dry eye syndrome can lead to scarring or ulceration of the cornea, infection and possible vision loss.

Dry eye syndrome results from any of a variety of etiologies. The approximately 10 million Americans afflicted with dry eye syndrome include those with normal aging of the tear glands as well as nearly 75% of individuals over the age of 65. Dry eye syndrome is most common in women who are pregnant or postmenopausal; individuals suffering from allergies or wearing contact lenses; and in patients with Sjögren's syndrome.

A bioartificial lacrimal gland of the invention can be implanted into any of several anatomical regions of the eye including, without limitation, substantially upon the outer surface of the eye or episclerally, for example, over an avascular region. As a non-limiting example, a bioartificial lacrimal gland of the invention can be implanted substantially upon the outer surface of the eye and anchored in the sclera. In one embodiment, a bioartificial lacrimal gland of the invention is implanted in the conjunctiva, which is the mucous membrane lining the anterior surface of the eyeball and the posterior surface of the eyelids. In another embodiment, a bioartificial lacrimal gland of the invention is implanted in the supero-temporal conjunctiva and optionally anchored in the sclera. In a further embodiment, a bioartificial lacrimal gland of the invention is implanted into the supero-temporal conjunctiva and optionally anchored into one or more orbital bones. In still another embodiment, a bioartificial lacrimal gland which is implanted into the supero-temporal conjunctiva and anchored into the sclera or orbital bones includes a common duct that egresses at the conjunctival surface of the eye.

One skilled in the art understands that a bioartificial gland of the invention can be positioned, for example, close to the native lacrimal gland such that the one or more outlets, or a common duct if present, is localized relatively close to the tear film. In one embodiment, the one or more outlets, or a common duct if present, exits underneath the upper eyelid. If desired, fluid can be directed from one or more outlets or a common duct of the bioartificial gland to the conjunctival surface by forming holes or tunnels through layers of the sclera or other tissue, directing the fluid outflow to the conjunctival surface. Such holes can be formed by surgical procedures well known in the art or through application of a permeability enhancing agent such as ethanol, oleic acid, isopropyl myristate or the like.

A variety of techniques suitable for ocular implantation are well known in the art and include, without limitation, surgical means, injection and trocar. As an example, a bioartificial lacrimal gland of the invention can be implanted, for example, using an implanter as described, for example, in U.S. Pat. Nos. 3,921,632 or 4,451,254. The mobility of a bioartificial lacrimal gland of the invention can optionally be reduced or prevented by anchoring, which can be performed by any of a variety of routine techniques including, but not limited to, suturing or cellular ingrowth into an anchoring orbital bone or artificial plate.

One skilled in the art understands that a bioartificial lacrimal gland of the invention optionally can include one or more additional components. Such components can have a biological activity which promotes, without limitation, immunosuppression; vascularization; cell growth; cell adhesion; stability or resistance to movement; or tissue ingrowth into the implanted bioartificial lacrimal gland. Such components include, yet are not limited to, naturally and non-naturally occurring biological, chemical and pharmaceutical agents such as immunosuppressive agents; pro-angiogenic agents; soluble growth factors and inhibitors; cell adhesion peptides; endothelial cells; and feeder cells. Such components can be included within any portion of the bioartificial lacrimal gland including, without limitation, the housing interior; interior surface of the permeable housing; within the viscous substratum; incorporated within the permeable housing itself; adhered to or associated with the external surface of the permeable housing or unit support; or otherwise included within or stably associated with the bioartificial lacrimal gland. As one example, biodegradable supports which promote vascularization following implantation have been described for use in tissue engineering (Mooney et al., *Cell Transplant.* 3:203-210 (1994)). As another non-limiting example, a component which promotes resistance of the bioartificial gland to movement or which promotes tissue ingrowth, or both, can be adhered to the external surface of the permeable housing or unit support or otherwise attached to the exterior of the permeable housing or unit support, or indirectly attached to a portion of the bioartificial lacrimal gland.

In one embodiment, a bioartificial lacrimal gland of the invention includes an immunosuppressive agent. Such an immunosuppressive agent can be useful, for example, when a bioartificial lacrimal gland is implanted into a patient with an elevated risk of immunological rejection or who exhibits one or more symptoms consistent with immunological rejection, or in conjunction with a bioartificial lacrimal gland which is not encapsulated by a membrane, or as a precautionary measure especially where unmatched allogeneic or xenogeneic lacrimal epithelial cells are used. As described further below, one skilled in the art understands that immunosuppressive agents useful in the invention include those which are incorporated within a bioartificial lacrimal gland as well as those administered systemically or locally at the same or a different site as the site of gland implantation.

A variety of immunosuppressive agents can be useful in the bioartificial lacrimal glands and methods of the invention. Such immunosuppressive agents encompass, without limitation, steroids such corticosteroids, prednisolone acetate, cyclosporin and tacrolimus (FK506); and therapeutic monoclonal antibodies such as anti-T lymphocyte, anti-CD4+, anti-ICAM-1 and anti-IL-2 antibodies. Such immunosuppressive agents further include, yet are not limited to, cyclophosphamide, azathioprine, prednisone, methylprednisone, prostaglandins and other steroids.

An attachment surface also can be useful in a bioartificial lacrimal gland of the invention. Such an attachment surface can be included, for example, on the external surface of the permeable housing or unit support in order to promote tissue ingrowth, thereby stabilizing and maintaining the bioartificial lacrimal gland at a fixed location following implantation. The composition and spacing of the one or more attachment surfaces generally promote cellular ingrowth and provide resistance to both proximal and distal axial migration of the bioartificial gland. As non-limiting examples, where the permeable housing is a tube having a first closed end and a second end which is the outlet connecting the housing interior to the housing exterior, an attachment surface that promotes tissue ingrowth can be positioned proximally of the closed end, throughout the length of the tube, concentrically around the tube, or can cover essentially the entire external surface of the tube. In one embodiment, the attachment surface is a porous surface which promotes cellular ingrowth; the porosity of the cell ingrowth surface can be, for example, in the range of 0.2 µm to 100 µm or greater, for example, in the range of 0.2 µm to 50 µm or in the range of 0.2 µm to 20 µm. Suitable materials which promote tissue ingrowth include, yet are not limited to, polytetrafluoroethylene (PTFE); polyethylene terephthalate; polyester; polyurethane; silicone; dacron; and polypropylene knit. In one embodiment, a bioartificial lacrimal gland of the invention includes PTFE with a 0.22 µm pore size, allowing shallow ingrowth into the bioartificial gland and preventing axial migration of the gland along tissue planes.

A pro-angiogenic agent also can be optionally included in a bioartificial lacrimal gland of the invention. Pro-angiogenic agents are well known in the art as described, for example, in Folkman and Klagsbrun, *Science,* 235:442-447 (1987), and include, without limitation, agents which act predominantly or solely upon endothelial cells such as vascular endothelial growth factors (VEGFs). Pro-angiogenic agents useful in a bioartificial lacrimal gland of the invention include naturally occurring and synthetic angiogenic growth factors and cytokines that induce or promote the growth of new blood vessels by stimulating endothelial cell growth or migration and encompass, without limitation, isoforms of vascular endothelial growth factor (VEGF) such as VEGF-A, including $VEGF_{121}$ and $VEGF_{165}$, and various forms of fibroblast growth factor including, but not limited to, FGF-1 and FGF-2.

VEGF-A, also known as vascular permeability factor (VPF), as well as VEGF-B, VEGF-C and VEGF-D, can be useful in a bioartificial lacrimal gland of the invention. Exemplary pro-angiogenic agents useful in a bioartificial lacrimal gland of the invention include, without limitation, the recombinant 165 kDa isoform of VEGF, designated rhVEGF, developed by Genentech; a nucleic acid molecule encoding the 121 amino acid isoform of VEGF (BIOBYPASS™; GenVec/ Parke Davis); and nucleic acids encoding VEGF-B, VEGF-C and VEGF-D. See, for example, Miller and Abrams, *Gen. Engin. News* 18:1 (1998).

Pro-angiogenic agents useful in a bioartificial lacrimal gland of the invention further include, without limitation, members of the fibroblast growth factor family such as FGF-1 (acidic), FGF-2 (basic), FGF-4 and FGF-5 (Slavin et al., *Cell Biol. Int.* 19:431-444 (1995); and Folkman and Shing, *J. Biol. Chem.* 267:10931-10934 (1992)). A fibroblast growth factor useful in the invention can be, without limitation, FIBLAST®

(trafermin), a recombinant form of FGF-2 being developed by Scios, Inc. (Mountain View, Calif.) and Wyeth Ayerst Laboratories (Radnor, Pa.); or GENERX™, an adenoviral gene therapy vector encoding FGF-4 developed by Collateral Therapeutics (San Diego, Calif.) and Schering A G (Miller and Abrams, supra, 1998). Pro-angiogenic agents useful in the invention further include, yet are not limited to, angiopoietin-1, an angiogenic factor that signals through the endothelial cell-specific Tie2 receptor tyrosine kinase (Davis et al., Cell 87:1161-1169 (1996); and Suri et al., Cell 87:1171-1180 (1996)). One skilled in the art understands that these and other pro-angiogenic agents, which can be delivered as protein or nucleic acid therapeutics, can be useful in the bioartificial lacrimal glands and methods of the invention.

A variety of additional components, including those with biological activity, also can be optionally included in a bioartificial lacrimal gland of the invention. As one non-limiting example, endothelial cells can be included in the gland to engineer a vascular network. See, for example, Holder et al., Tissue Engineering 3:149-160 (1997). As another non-limiting example, a soluble growth factor such as epidermal growth factor (EGF) or nerve growth factor (NGF) can be included in a bioartificial lacrimal gland of the invention. The use of growth factors in tissue engineering is well known in the art as described, for example, in Mooney et al., Biotech. Bioeng. 50:442-449 (1996). As a further non-limiting example, cell adhesion, which is generally dependent on the presence of specific cell-surface receptors such as integrins, can be enhanced by inclusion of a cell-adhesion promoting agent such as a cell adhesion peptide as described, for example, in Hubbell, Biotech. 13:565-576 (1995).

The methods of the invention optionally include separate systemic or local administration of an immunosuppressive agent, pro-angiogenic agent or other therapeutic agent or component with biological activity. Useful routes of systemic or local administration encompass, without limitation, oral administration; intravenous injection; intraperitoneal injection; intramuscular injection; subcutaneous injection; transdermal diffusion or electrophoresis; topical eye-drops or ointments; periocular or intraocular injection including subconjunctival injection; extended release delivery devices including locally implanted extended release devices; and intraocular or periocular implants including bioerodible and reservoir-based implants which are separate from the bioartificial lacrimal gland. Furthermore, where the immunosuppressive agent, pro-angiogenic agent or other therapeutic agent or component with biological activity is a nucleic acid molecule, one of various methods known in the art of gene therapy can be utilized. Such methods include, but are not limited to, ballistic gun delivery, adenoviral transformation, lentiviral transformation, cytomegaloviral transformation, microinjection and electroporation as described further below.

As non-limiting examples, a corticosteroid immunosuppressive agent can be incorporated within a bioartificial lacrimal gland of the invention or administered topically, periocularly, systemically, or as a slow-release formulation, or using multiple routes of administration. As one example, prednisolone acetate can be administered topically as a 1% preparation. Topical prednisolone acetate can be applied hourly for mild reactions combined with intravenous methylprednisolone pulse therapy (3 to 5 mg/kg IV push) and followed by five days of oral prednisone (1 mg/kg/day) for severe reactions. A single dose of intravenous methylprednisolone (500 mg) can be substituted, if desired, for daily oral prednisone (60 to 80 mg) when combined with topical therapy. One skilled in the art understands that these and other corticosteroid immunosuppressive agents can be useful in the methods of the invention.

The immunosuppressive agent cyclosporin also can be useful in the methods of the invention and can be administered, for example, systemically for a period of months or years or administered topically, for example, as a 2% cyclosporin formulation. Therapeutic monoclonal antibodies also can be useful in the methods of the invention; for example, anti-T lymphocyte or other immunosuppressive monoclonal antibodies can be administered intracamerally. It is understood that these and other immunosuppressive agents can be administered to the individual receiving a bioartificial lacrimal gland of the invention. It is further understood that separate administration of an immunosuppressive agent can be prior to, during, or subsequent to implantation of the bioartificial lacrimal gland, and that an immunosuppressive agent can be administered once or repeatedly as needed.

Immunosuppressive agents, pro-angiogenic agents and other nucleic acid therapeutics can be administered by established gene transfer techniques including ballistic gun delivery (see, for example, Tanelian et al., BioTechniques 23:484-488 (1997)). In this method, 0.2-0.5 mg gold particles are coated with plasmid DNA, which is then delivered into the cornea using a ballistic gun. The depth of delivery of the plasmid DNA is a function of the pressure of the gun, thus facilitating delivery of plasmid DNA to a desired depth. A lentivirus also can be used to administer an immunosuppressive agent, pro-angiogenic agent or other nucleic acid therapeutic agent in a method of the invention, for example, essentially as described in Wang et al., Gene Therapy 7:196-200 (2000). Corneal endothelial cells, epithelial cells and stromal keratocytes in human cornea can be exposed to a lentivirus that includes the desired nucleic acid molecule for transduction in vitro or in situ. An adenovirus also can be used to administer an immunosuppressive agent, pro-angiogenic agent or other nucleic acid therapeutic to the eye in vivo using procedures which are well known in the art. (See, for example, U.S. Pat. No. 5,827,702).

Microinjection and electric pulse also can be useful for administering an immunosuppressive agent, pro-angiogenic agent or other nucleic acid therapeutic to an individual receiving a bioartificial lacrimal gland. Microinjection and electric pulse can be used, for example, to introduce cytomegalovirus, or a plasmid expression vector, into cornea essentially as described in Sakamoto et al., Hum. Gene Ther. 10:2551-2557 (1999), or Oshima et al., Gene Therapy 5:1347-1354 (1998). Injection of virus or plasmid into the anterior chamber at the limbus, followed by electric pulses, results in transduction of corneal endothelial cells. One skilled in the art understands that these and other established gene therapy techniques can be useful in the methods of the invention.

The following example is intended to illustrate but not limit the present invention.

EXAMPLE I

Preparation and Characterization of a Bioartificial Lacrimal Gland

A. Isolation of Rabbit Lacrimal Epithelial Cells and Preparation of a Bioartificial Lacrimal Gland Rabbits used for isolation of lacrimal epithelial cells are adult, female, New Zealand Whites (Irish Farms; Norco, Calif.), weighing approximately 4.0 kg. Animals are narcotized with a mixture of 1 to 1.5 ml ketaset (100 mg ml$^{-1}$) and xylazine (100 mg ml$^{-1}$), and euthanized with an overdose of Eutha-6CII (120 mg ml−1). All standards and procedures for the proper care and use of animals are as described in the Guiding Principles in the Care and Use of Animals (DHEW publication, NIH 80-23) and the ARVO Resolution on the Use of Animals in Research.

Purified rabbit lacrimal acinar cells are prepared essentially as described in Guo et al., *Exp Eye Res.* 71: 11-22 (2000), to yield a cell population composed of approximately 98% lacrimal acinar cells. Briefly, inferior lacrimal glands are removed aseptically, placed in a dish with Ham's medium and finely minced between scalpel blades. Tissue fragments are then washed and enzymatically digested with a combination of collagenase, DNAse, and hyaluronidase. Gland digests are centrifuged, washed twice, and subsequently filtered through a 70-μm nylon filter followed by a 10-μm filter, and further centrifuged in a Ficoll gradient. The cellular fraction is subsequently transferred to HEPATO STIM® Culture Medium (HSM; Becton Dickinson, Bedford, Mass.), which is a defined serum-free culture medium based upon the original Williams E medium (Williams and Gunn, *Exp Cell Res.* 89:139-42 (1974); Sinclair et al., *Cancer Res.* 50:5219-24 (1990)) supplemented with dexamethasone and ITS+ Universal Culture supplement, a proprietary concentrated formulation of hormones and metabolites. Just prior to use, 5 ng ml$^{-1}$ epidermal growth factor and 10% fetal bovine serum are added to the HEPATO STIM® Culture Medium. The medium is further supplemented with 2 mM L-glutamine, 100 U ml$^{-1}$ penicillin, 100 μg ml$^{-1}$ streptomycin, and 0.25 μg ml$^{-1}$ fungizone prior to use.

A tubular permeable housing with a viscous substratum including MATRIGEL™ is prepared essentially as follows. MATRIGEL™, which is soluble at 4° but forms a gel at 37°, is thawed overnight on ice in a refrigerator and, immediately before use, diluted into cold HEPATO STIM® Culture Medium containing 10% fetal bovine serum (Omega Scientific, Inc.; Tarzana, Calif.) and 5 ng/ml epidermal growth factor. The final working concentration of MATRIGEL™ for use in applying the viscous substratum to the tubular permeable housing is approximately 1 mg/ml.

The MATRIGEL™ solution is applied into a doubly open-ended tubular permeable housing essentially as follows. The doubly open-ended permeable housing is perfused at 4° with a solution of MATRIGEL™ diluted in HEPATO STIM® Culture Medium and subsequently briefly perfused with media that does not contain MATRIGEL™. The unstirred fluid layer adjacent to the interior surface of the tubular permeable housing contains the MATRIGEL™ solution. Upon transfer of the tubular permeable housing to a 37° water bath, MATRIGEL™ lines the interior wall of tubular permeable housing while the lumen of the housing remains patent.

Lacrimal epithelial cells are subsequently applied into the interior of the MATRIGEL™-lined tubular permeable housing as follows. A suspension of the lacrimal epithelial cells is perfused through the permeable housing; such a cell population is suspended in HEPATO STIM® Culture Medium (HSM) and perfused at 37° C. or suspended in dilute MATRIGEL™ and perfused at 4° C., then warmed to 37° C.

Figure 1B:
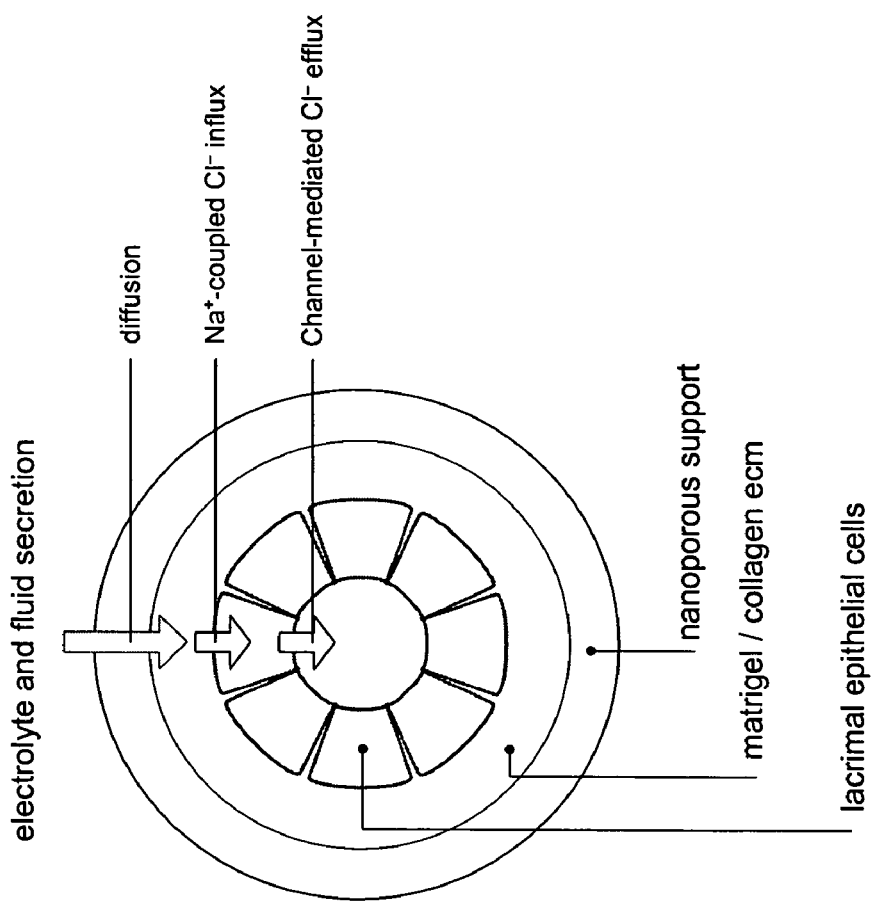

Gland units prepared as described above, including, for example, the unit illustrated in FIG. 1, are maintained at 37° C. with 5% CO$_2$ until termination of the sampling period. The external bathing medium is replaced about every seven days.

B. Morphological Characterization of Individual Tubes of a Bioartificial Lacrimal Gland Using Electron and Confocal Microscopy Lacrimal epithelial cells within the gland unit are examined by confocal and electron microscopy to determine the morphology of the acinar cells. The presence of tight junctions is assessed by electron microscopy (EM) and by confocal immunofluorescence microscopic analysis of the expression and localization of one or more of the principal tight junction-associated proteins as described further below.

In particular, at the end of each sampling period, the gland units are immersed in a fixative of 2% formaldehyde, 2% glutaraldehyde and 0.02% calcium chloride in 0.1 M cacodylate buffer, pH 7.4. After fixation for one hour, the units are rinsed in cacodylate buffer and post-fixed in 1% osmium tetroxide and 0.02% calcium chloride in 0.1 M cacodylate buffer, pH 7.4, for an additional hour. Some samples are stained en bloc with 1% tannic acid, rinsed in 0.1 M cacodylate buffer (pH 6.8), dehydrated in a graded series of ethanol rinses, and subsequently infiltrated and embedded in LR White. Sections are collected for confocal microscopy using a Zeiss LSM 510 confocal microscope, and additional sections are collected for electron microscopy and stained with uranyl acetate and lead citrate prior to analysis with a JEOL 1200 EX TEM microscope.

Sections are stained with rabbit anti-B-catenin, anti-ZO-1, anti-occludin, anti-claudin 1, and anti-claudin 2 antibodies (Zymed; South San Francisco, Calif.) according to the manufacturer's instructions. Analysis of expression of ZO-1, β-catenin, occludin, claudin 1, and claudin 2 is performed by confocal microscopy essentially as described in Aframian et al., supra, 2002, using a Bio-Rad (Hercules, Calif.) 1024 laser scanning confocal imaging system.

Figure 3:
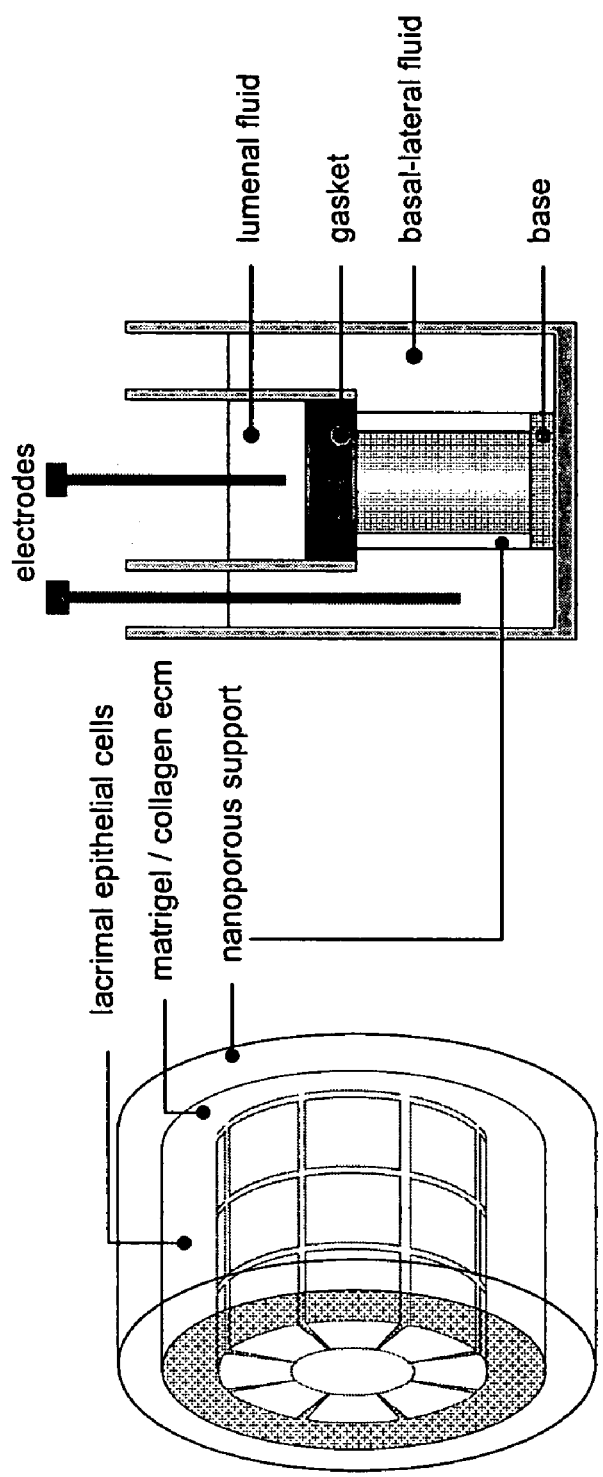
FIG. 3 shows a schematic diagram illustrating a chamber suitable for physical, electrical and optical sampling of the luminal fluid from a bioartificial lacrimal gland.

C. Functional Characterization of Individual Units of a Bioartificial Lacrimal Gland Protein secretion and electrophysiological activity of the gland units are assessed essentially as follows to confirm that the gland unit transports fluid from the extracellular space and secretes protein as does a native lacrimal gland in situ. A chamber suitable for physical, electrical, and optical sampling of the lumenal fluid is illustrated in FIG. 3. Such a chamber is a hybrid of two classic systems, the Costar Transwell and the stopped flow, perfused renal tubule. In a first configuration, lumenal fluid enters a chamber which is electrically isolated from the basal-lateral fluid, and transepithelial resistance and transepithelial potential difference are measured (see FIG. 4A). The bioelectrical properties are measured for both an unstimulated unit of the bioartificial gland and a unit stimulated by addition of 100 μM carbachol to the basal-lateral bathing fluid using a Millicell ERS epithelial volt-ohmmeter (Millipore; Allen, Tex.) as described by the manufacturer. Transepithelial electrical resistance (TER) readings are obtained by subtracting readings from control units lacking cells from readings obtained with complete gland units seeded with cells.

Figure 4:
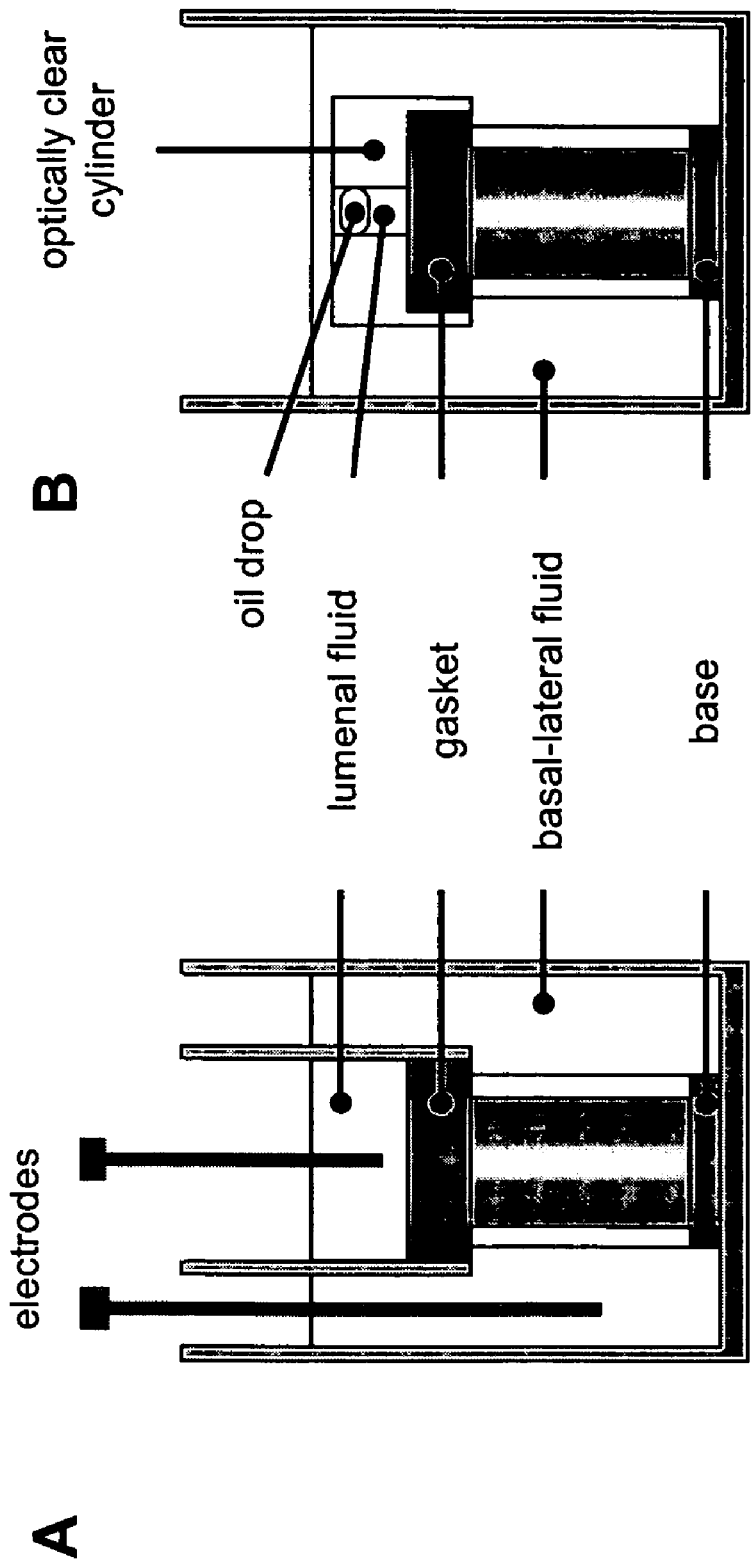
FIG. 4 shows alternate configurations of the chamber shown in FIG. 3. (A) Transepithelial resistance and transepithelial potential difference are measured following entry of lumenal fluid into a chamber which is electrically isolated from the basal-lateral fluid. (B) Fluid secretion is measured following entry of lumenal fluid into an optically clear tube.

In a second configuration, lumenal fluid enters an optically clear tube, and fluid secretion is measured (see FIG. 4B). Fluid secretion is calculated from the optically measured displacement of an oil drop placed in the clear tube. Again, one analyzes both an unstimulated unit of the bioartificial gland and a unit stimulated by addition of 100 μM carbachol to the basal-lateral bathing fluid.

In a variation of the second configuration, β-hexosaminidase secretion is assessed. Optically clear tubes are placed at both ends of the gland unit in order to perfuse the lumen with micropipettes. The system is incubated under stopped flow conditions for measured intervals in the absence of carbachol, and the lumenal fluid collected and replaced. At the end of each incubation period, fluid from the lumen of the gland unit is removed and assayed for β-hexosaminadase activity using the reaction described by Barret and Heath in Dingle (Ed.), *Lysosomes: A Laboratory Handbook* Elsevier/North-Holland Biomedical Press, Amsterdam, 1977, modified for analysis using a 96-well black walled microtiter plate and fluorescent microplate reader. The stopped flow incubation is subsequently repeated with 100 µM carbachol present in the lumenal bathing fluid.

All journal article, reference and patent citations provided above, in parentheses or otherwise, whether previously stated or not, are incorporated herein by reference in their entirety.

Although the invention has been described with reference to the example provided above, it should be understood that various modifications can be made without departing from the spirit of the invention. Accordingly, the invention is limited only by the claims.

What is claimed is:

1. A bioartificial lacrimal gland, comprising at least one unit, said unit comprising
    (a) a permeable housing having an interior and an exterior;
    (b) an outlet connecting the housing interior to the housing exterior;
    (c) a population of lacrimal epithelial cells within the housing interior, wherein said gland is characterized by directional fluid secretion in which fluid exits from said housing interior to said housing exterior through said outlet; and
    (d) a gate joined to said outlet.

2. The bioartificial lacrimal gland of claim 1, wherein fluid exits from said interior through said outlet at a rate of at least 6.5 µl/cm²/hour.

3. The bioartificial lacrimal gland of claim 1, further comprising a viscous substratum within the housing interior.

4. The bioartificial lacrimal gland of claim 1, said permeable housing having a concave interior surface.

5. The bioartificial lacrimal gland of claim 4, said permeable housing having a substantially cylindrical interior surface.

6. The bioartificial lacrimal gland of claim 4, said permeable housing having a substantially spherical interior surface.

7. The bioartificial lacrimal gland of claim 5, wherein said permeable housing is substantially tubular.

8. The bioartificial lacrimal gland of claim 7, wherein said substantially tubular permeable housing is a tube.

9. The bioartificial lacrimal gland of claim 8, said tube having a first closed end and a second end which is said outlet.

10. The bioartificial lacrimal gland of claim 1 or claim 9, wherein said permeable housing is a porous housing.

11. The bioartificial lacrimal gland of claim 10, wherein said porous housing has a pore size of between 0.01 and 10 microns.

12. The bioartificial lacrimal gland of claim 11, wherein said pore size is between 0.1 and 5 microns.

13. The bioartificial lacrimal gland of claim 1 or claim 5, wherein said permeable housing comprises a polymeric biomaterial.

14. The bioartificial lacrimal gland of claim 13, wherein said polymeric biomaterial is a homopolymeric biomaterial.

15. The bioartificial lacrimal gland of claim 13, wherein said polymeric biomaterial is a copolymeric biomaterial.

16. The bioartificial lacrimal gland of claim 1 or claim 9, wherein said permeable housing comprises a non-biodegradable biomaterial.

17. The bioartificial lacrimal gland of claim 1 or claim 9, wherein said permeable housing comprises a biodegradable biomaterial.

18. The bioartificial lacrimal gland of claim 1 or claim 9, wherein said permeable housing is a porous housing.

19. The bioartificial lacrimal gland of claim 18, wherein said porous housing is a porous membrane.

20. The bioartificial lacrimal gland of claim 1 or claim 9, wherein said permeable housing comprises a biomaterial selected from the group: polysiloxane; polydimethylsiloxane; polyurethane; polyvinylpyrrolidone; polymethacrylate; polyvinyl alcohol; polyethylene; polyethylene glycol; poly(glycolic acid); poly(L-lactic acid); poly(lactic-co-glycolic acid); collagen; cellulose; and a copolymer or derivative thereof.

21. The bioartificial lacrimal gland of claim 20, said permeable housing comprising at least 90% of a single biomaterial selected from the group: polysiloxane; polydimethylsiloxane; polyurethane; polyvinylpyrrolidone; polymethacrylate; polyvinyl alcohol; polyethylene; polyethylene glycol; poly(glycolic acid); poly(L-lactic acid); poly(lactic-co-glycolic acid); collagen; cellulose; and a copolymer or derivative thereof.

22. The bioartificial lacrimal gland of claim 9, wherein said tube has a lumen of uniform diameter.

23. The bioartificial lacrimal gland of claim 22, wherein said lumen has a diameter of no more than 2 mm.

24. The bioartificial lacrimal gland of claim 23, wherein said lumen has a diameter of between 0.1 and 0.5 mm.

25. The bioartificial lacrimal gland of claim 9, 22, 23 or 24, wherein said tube has a length of at most 10 mm.

26. The bioartificial lacrimal gland of claim 25, wherein said tube has a length of at most 5 mm.

27. The bioartificial lacrimal gland of claim 3, wherein said viscous substratum is adhered to the interior surface of said permeable housing.

28. The bioartificial lacrimal gland of claim 26, wherein said viscous substratum is a gel.

29. The bioartificial lacrimal gland of claim 28, wherein said gel is a hydrogel.

30. The bioartificial lacrimal gland of claim 27 or 29, where said viscous substratum comprises a biomaterial selected from the group collagen, hydroxymethylcellulose, hyaluronan and a copolymer or derivative thereof 31. The bioartificial lacrimal gland of claim 26 or 29, where said viscous substratum comprises one or more extracellular matrix components.

32. The bioartificial lacrimal gland of claim 31, wherein said viscous substratum comprises Matrigeltm™.

33. The bioartificial lacrimal gland of claim 32, wherein said viscous substratum comprises Matrigeltm™ at a final concentration of 0.25 to 5 mg/ml.

34. The bioartificial lacrimal gland of claim 28, wherein said viscous substratum further comprises fetal bovine serum.

35. The bioartificial lacrimal gland of claim 1 or claim 9, wherein said lacrimal epithelial cells are arrayed in a polarized monolayer.

36. The bioartificial lacrimal gland of claim 35, wherein said polarized monolayer is adhered to said viscous substratum.

37. The bioartificial lacrimal gland of claim 1 or claim 9, wherein said lacrimal epithelial cells are selected from the group primary cells, established cells, transfected cells, human cells, primate cells, rabbit cells, and goose cells.

38. The bioartificial lacrimal gland of claim 37, wherein said lacrimal epithelial cells are human cells.

39. The bioartificial lacrimal gland of claim 37, wherein said lacrimal epithelial cells are rabbit cells.

40. The bioartificial lacrimal gland of claim 1 or claim 9, wherein said lacrimal epithelial cells express an exogenous nucleic acid molecule.

41. The bioartificial lacrimal gland of claim 40, wherein said exogenous nucleic acid molecule encodes a receptor.

42. The bioartificial lacrimal gland of claim 1 or claim 9, said gland further comprising at least one growth factor.

43. The bioartificial lacrimal gland of claim 42, wherein said growth factor is selected from the group Hepato Stim® Culture Medium and epidermal growth factor.

44. The bioartificial lacrimal gland of claim 42, wherein said growth factor is Hepato Stim® Culture Medium.

45. The bioartificial lacrimal gland of claim 42, comprising fetal bovine serum at a concentration of 10% and epidermal growth factor at a concentration of 5 ng/ml.

46. The bioartificial lacrimal gland of claim 1 or claim 9, said gland further comprising an immunosuppressive agent.

47. The bioartificial lacrimal gland of claim 1, wherein said gate is responsive to a stimulus.

48. The bioartificial lacrimal gland of claim 1 or claim 9, further comprising an encapsulating membrane, said membrane impermeable to antibodies and immune cells.

49. The bioartificial lacrimal gland of claim 1 or claim 9, said gland comprising a plurality of units.

50. The bioartificial lacrimal gland of claim 49, said gland comprising at least three units.

51. The bioartificial lacrimal gland of claim 49, said gland comprising at least five units.

52. The bioartificial lacrimal gland of claim 49, further comprising a unit support which holds each of said plurality of units in a defined configuration.

53. The bioartificial lacrimal gland of claim 52, wherein each of said units is held substantially in parallel.

54. The bioartificial lacrimal gland of claim 49, further comprising an encapsulating membrane, said membrane impermeable to antibodies and immune cells.

55. The bioartificial lacrimal gland of claim 49, wherein said permeable housing is a tube.

56. The bioartificial lacrimal gland of claim 55, said tube having a first closed end and a second end which is said outlet.

57. The bioartificial lacrimal gland of claim 56, further comprising a common duct, each of said outlets of said tubes being joined to said common duct.

58. The bioartificial lacrimal gland of claim 50, said common duct further comprising a gate.

59. The bioartificial lacrimal gland of claim 50, said common duct further comprising a gate.

60. The bioartificial lacrimal gland of claim 50, wherein said gate is responsive to a stimulus.

* * * * *

UNITED STATES PATENT AND TRADEMARK OFFICE
CERTIFICATE OF CORRECTION

PATENT NO. : 7,547,447 B2  Page 1 of 1
APPLICATION NO. : 10/990359
DATED : June 16, 2009
INVENTOR(S) : Samuel C. Yiu et al.

It is certified that error appears in the above-identified patent and that said Letters Patent is hereby corrected as shown below:

In Column 30, Line 41:    Claim 32: Replace "Matrigeltm™", with -- Matrigel™ --

In Column 30, Line 43:    Claim 33: Replace "Matrigeltm™", with -- Matrigel™ --

In Column 32, Lines 18-19:   Replace "claims 59", with -- The bioartificial lacrimal gland of claim 58 further comprising an encapsulating membrane, said membrane impermeable to antibodies and immune cells --

Signed and Sealed this
First Day of May, 2012

David J. Kappos
*Director of the United States Patent and Trademark Office*